United States Patent
Love et al.

(10) Patent No.: US 11,957,881 B2
(45) Date of Patent: Apr. 16, 2024

(54) THERAPY DEVICES, METHODS, AND SYSTEMS INCLUDING A PISTON-STYLE DETECTOR

(71) Applicant: BIGFOOT BIOMEDICAL, INC., Milpitas, CA (US)

(72) Inventors: John Love, San Diego, CA (US); Adam Joseph Livingston, Oceanside, CA (US); George Crothall, Oceanside, CA (US); Jeffrey Johnson, San Diego, CA (US); Sarah Matarese, San Jose, CA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 559 days.

(21) Appl. No.: 17/052,653

(22) PCT Filed: May 2, 2019

(86) PCT No.: PCT/US2019/030384
§ 371 (c)(1),
(2) Date: Nov. 3, 2020

(87) PCT Pub. No.: WO2019/213385
PCT Pub. Date: Nov. 7, 2019

(65) Prior Publication Data
US 2021/0236735 A1    Aug. 5, 2021

Related U.S. Application Data

(60) Provisional application No. 62/667,085, filed on May 4, 2018, provisional application No. 62/667,111, filed on May 4, 2018.

(51) Int. Cl.
*A61M 5/315* (2006.01)
*A61M 5/32* (2006.01)
*A61M 5/31* (2006.01)

(52) U.S. Cl.
CPC .......... *A61M 5/315* (2013.01); *A61M 5/3202* (2013.01); *A61M 2005/3125* (2013.01);
(Continued)

(58) Field of Classification Search
CPC ................ A61M 5/315; A61M 5/3202; A61M 2005/3125; A61M 2202/0486;
(Continued)

(56) References Cited

U.S. PATENT DOCUMENTS 8,206,340 B2    6/2012    Arefieg
8,556,866 B2    10/2013    Krulevitch et al.
(Continued)

FOREIGN PATENT DOCUMENTS

EP    2879740    3/2017
JP    2013-530004 A    7/2013
(Continued)

OTHER PUBLICATIONS

The extended European search report issued for European Patent Application No. 19795783.0, dated Apr. 25, 2022, 12 pages.
(Continued)

*Primary Examiner* — Emily L Schmidt
*Assistant Examiner* — Nelson Louis Alvarado, Jr.
(74) *Attorney, Agent, or Firm* — Hamre, Schumann, Mueller & Larson, P.C.

(57) ABSTRACT

A pen cap for a medication delivery pen includes a piston-style detector mechanism. The piston-style detector mechanism includes at least an inner shell having first open end through which the medication delivery pen can be inserted, a second end opposite the first end, a sidewall defined by an outer surface and an opposing inner surface, and a passageway extending from the outer surface to the inner surface. The sidewall extends between the first end and the second end thereby defining a pen-receiving cavity there between.
(Continued)

The piston-style detector mechanism further includes at least one switch and a translatable shaft at least partially disposed in the passage. The translatable shaft includes a body that extends at least from a pen-interfacing portion in the pen-receiving cavity to a switch-interfacing portion thereof. The translatable shaft is oriented to travel from a first location to at least a second location during capping of a medical delivery pen into the inner shell to toggle the at least one switch.

20 Claims, 18 Drawing Sheets

(52) U.S. Cl.
CPC ............... *A61M 2202/0486* (2013.01); *A61M 2205/3553* (2013.01); *A61M 2230/201* (2013.01)

(58) Field of Classification Search
CPC .... A61M 2205/3553; A61M 2230/201; A61M 2005/2006; A61M 2205/18; A61M 2205/3523; A61M 2205/3569; A61M 2205/3584; A61M 2205/502; A61M 2205/52; A61M 2205/6081; A61M 2205/14; A61M 2205/3303; A61M 5/1723; A61M 5/31546; A61M 5/3213; A61B 5/0022; A61B 5/004; A61B 5/14532; A61B 5/4833
See application file for complete search history.

(56) References Cited

U.S. PATENT DOCUMENTS

| | | |
|---|---|---|
| 2011/0205083 A1 | 8/2011 | Janna et al. |
| 2014/0018733 A1 | 1/2014 | Sjolund et al. |
| 2014/0378801 A1* | 12/2014 | Poulsen ............ A61M 5/31525 604/189 |
| 2016/0034658 A1 | 2/2016 | Berman et al. |
| 2016/0263327 A1 | 9/2016 | Radmer et al. |
| 2017/0068799 A1* | 3/2017 | Mensinger ............. G16H 40/63 |
| 2017/0173262 A1 | 6/2017 | Veltz |
| 2017/0232204 A1* | 8/2017 | Knapp ................ A61M 5/5086 604/66 |
| 2018/0060529 A1 | 3/2018 | Crothall et al. |
| 2019/0175833 A1 | 6/2019 | Sjolund et al. |
| 2020/0327973 A1 | 10/2020 | Pryor et al. |

FOREIGN PATENT DOCUMENTS

| | | |
|---|---|---|
| WO | 2016/110592 | 7/2016 |
| WO | 2017/055468 | 4/2017 |
| WO | 2017/189712 | 11/2017 |
| WO | 2018/111776 | 6/2018 |

OTHER PUBLICATIONS

The partial supplementary European search report issued for European Patent Application No. 19795783.0, dated Dec. 23, 2021, 12 pages.
Office Action issued for Japanese Patent Application No. 2021-510279, dated Apr. 4, 2023, 10 pages including machine translation.
International Search Report and Written Opinion issued for PCT/US2019/030384, dated Jul. 11, 2019, 10 pages.

* cited by examiner

THERAPY DEVICES, METHODS, AND SYSTEMS INCLUDING A PISTON-STYLE DETECTOR

CROSS-REFERENCE TO RELATED APPLICATIONS

This application claims priority to U.S. Application Ser. Nos. 62/667,085, filed on May 4, 2018 and 62/667,111, filed on May 4, 2018. The disclosure of the prior applications are considered part of the disclosure of this application, and are incorporated in their entirety into this application.

FIELD

This invention relates to devices, methods, and systems including a piston-style detector. In particular embodiments, a piston-style detector can be located within a cap for a dosing device such as a medication delivery pen. Devices, methods, and systems provided herein can collect data about the timing of the removal and/or replacement of a cap from a dosing device, which can optionally be used to determine therapy settings and/or therapy recommendations.

BACKGROUND

Diabetes mellitus is a chronic metabolic disorder caused by an inability of a person's pancreas to produce sufficient amounts of the hormone insulin such that the person's metabolism is unable to provide for the proper absorption of sugar. This failure leads to hyperglycemia, i.e. the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Self-monitoring of blood glucose and the self-administration of insulin is the typical method for treating diabetes. The "correct" insulin dosage is a function of the level of glucose in the blood. Insufficient insulin dosages can result in hyperglycemia, and excessive insulin dosages can result in hypoglycemia, which can result in clumsiness, trouble talking, confusion, loss of consciousness, seizures, or death. Accordingly, people with diabetes (PWDs) face a considerable cognitive burden in determining appropriate doses of insulin.

Data collected about PWDs' therapy can be used to improve therapy decisions, thus there is a need for reliable and robust data collection tools.

SUMMARY

In an embodiment, there is a pen cap for a medication delivery pen, including a piston-style detector mechanism. The piston-style detector mechanism includes at least an inner shell having first open end through which the medication delivery pen can be inserted, a second end opposite the first end, a sidewall defined by an outer surface and an opposing inner surface, and a passageway extending from the outer surface to the inner surface. The sidewall extends between the first end and the second end thereby defining a pen-receiving cavity there between. The piston-style detector mechanism further includes at least one switch and a translatable shaft at least partially disposed in the passage. The translatable shaft includes a body that extends at least from a pen-interfacing portion in the pen-receiving cavity to a switch-interfacing portion thereof. The translatable shaft is oriented to travel from a first location to at least a second location during capping of a medical delivery pen into the inner shell to toggle the at least one switch.

In an embodiment there is a method for detecting capping of a medication delivery pen, including: capping the medication delivery pen with the pen cap that comprises the piston-style detector mechanism; during the capping, communicating a motion of the medication delivery pen to the translatable shaft of the piston-style detector mechanism so that the switch-interfacing portion interfaces with the switch to cause the toggling the switch.

In an embodiment there is a system that includes the pen cap that includes the piston-style detector mechanism, an analyte sensor system in communication with the pen cap, wherein the analyte sensor comprises: a blood glucose meter, a flash glucose monitor, or a continuous glucose monitor, and further comprising a mobile computing device, wherein the cap is in wireless communication with the mobile computing device.

Additional advantages of the embodiments will be set forth in part in the description which follows, and in part will be understood from the description, or may be learned by practice of the embodiments. The advantages will be realized and attained by means of the elements and combinations particularly pointed out in the appended claims.

It is to be understood that both the foregoing general description and the following detailed description are exemplary and explanatory only and are not restrictive of the embodiments, as claimed.

BRIEF DESCRIPTION OF THE DRAWINGS

The accompanying drawings, which are incorporated in and constitute a part of this specification, illustrate embodiments of the present teachings and together with the description, serve to explain the principles of the disclosure.

Figure 1A:
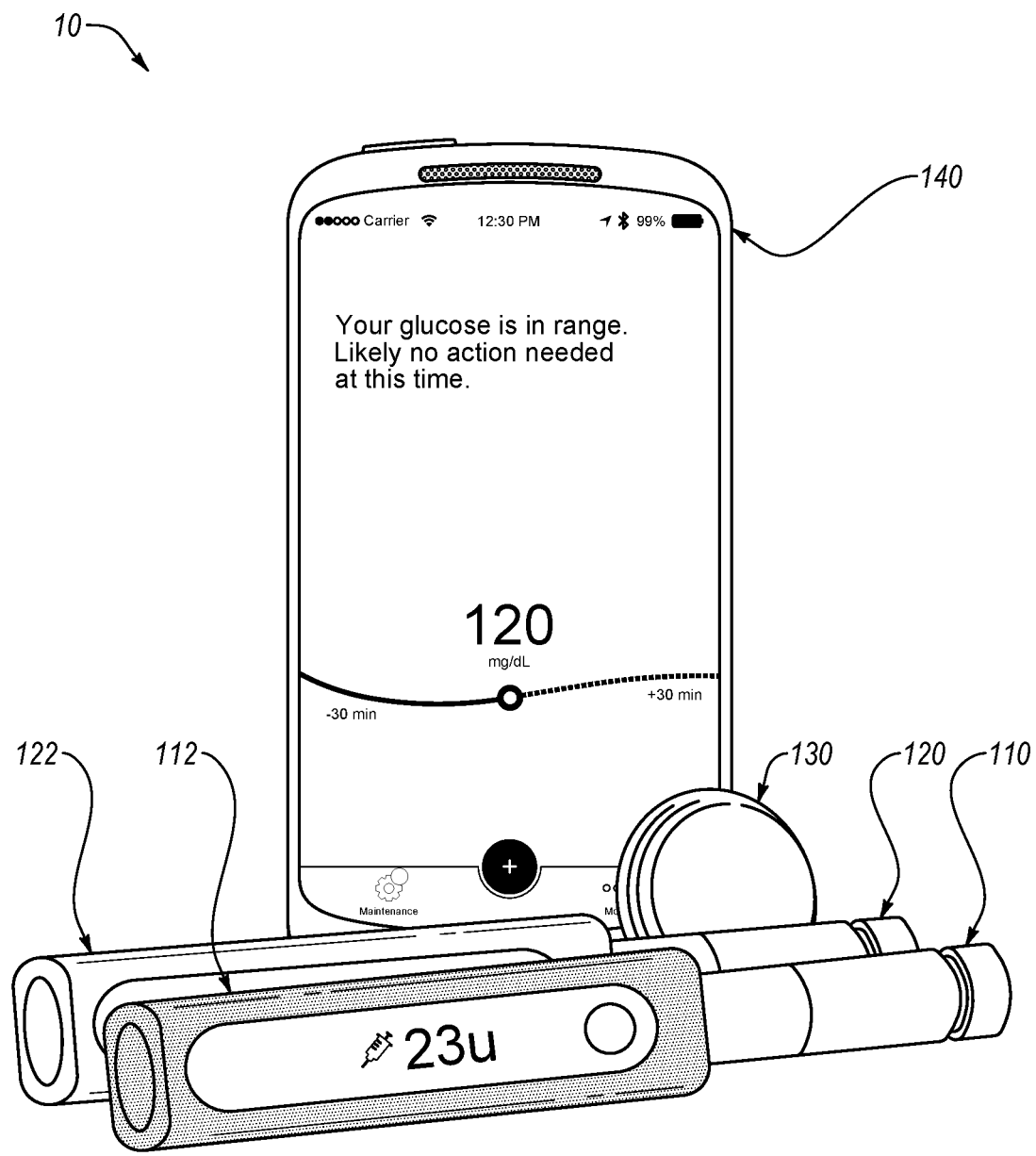
FIG. 1A illustrates a diabetes management system that may include an embodiment of a pen cap as described herein, insulin injection pens, a glucose sensor, and a mobile device.

It should be noted that some details of the figures have been simplified and are drawn to facilitate understanding of the present teachings rather than to maintain strict structural accuracy, detail, and scale.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

The following embodiments are described for illustrative purposes only with reference to the Figures. Those of skill in the art will appreciate that the following description is exemplary in nature, and that various modifications to the parameters set forth herein could be made without departing from the scope of the present embodiments. It is intended that the specification and examples be considered as examples only. The various embodiments are not necessarily mutually exclusive, as some embodiments can be combined with one or more other embodiments to form new embodiments. It will be understood that the structures depicted in the figures may include additional features not depicted for simplicity, while depicted structures may be removed or modified.

Pen caps provided herein can use any suitable technique to obtain pen capping information. In some cases, pen caps provided herein can include a piston-style detector mechanism comprising, among other things, a piston that extends into an injection-pen receiving inner shell of the pen cap and that comes into contact with an injection pen when an injection pen is inserted into the pen cap, and is pressed against a switch when the pen cap is secured to the injection pen.

In an exemplary embodiment of a therapy management system provided herein, FIG. 1A below illustrates a diabetes management system 10 that includes insulin injection pens 110 and 120, a glucose sensor 130, and a mobile device 140. The mobile device can be any suitable computing device such as a smartphone or a tablet. The mobile device can store and execute a mobile application that is adapted to display therapy relevant information wirelessly received from the other components of the system.

As shown, each insulin injection pen 110 and 120 includes a respective pen cap 112 and 122, each including a button and a display. In the embodiment shown in FIG. 1, the insulin pens can be commercially-available mechanical insulin pens that include any suitable insulin, including long-acting insulins and rapid-acting insulins (sometimes called quick-acting insulins or ultra-fast rapid-acting insulins). Suitable rapid-acting insulins include Humalog™, Novolog™, Apidra™, and Fiasp™. Suitable long-acting insulins include Lantus™, Levemir™, Toujeo™, and Tresiba™. As shown, insulin injection pen 110 represents an exemplary long-acting insulin pen and insulin injection pen 120 represents an exemplary rapid-acting insulin pen.

As shown, pen caps 112 and 122 can have distinct colors, shapes, or other indicia, which can be physical or digital, to assist a person with diabetes (PWD) in distinguishing the long-acting pen cap 112 from rapid-acting pen cap 122. The pens caps can be in wireless communication with the mobile device 140 so that data from the pens caps can be received and displayed by the mobile application.

The glucose sensor 130 can be any suitable glucose sensor, such as a blood glucose meter (BGM), and flash glucose sensor, or a continuous glucose sensor (CGM). In some cases, the glucose sensor can wirelessly transmit data when interrogated by a reader device (e.g., using NFC communication). In some cases, the glucose sensor 130 can wirelessly transmit data at predetermined intervals (e.g., using radio frequencies) using any suitable communication standard (e.g., BLE). In some cases, the glucose sensor 130 can transmit glucose data using multiple communication techniques. In some cases, the mobile device 140 and/or one or more of the insulin injection pens or pen caps can include an NFC reader adapted to obtain blood glucose data from the glucose sensor when brought within an interrogation distance of the glucose sensor. In some cases, the mobile device 140 and/or one or more of the insulin injection pens 110, 120 or pen caps 112, 122 can wirelessly receive blood glucose data broadcasted from the glucose sensor 130 at predetermined periods of time (e.g., every minute, every 5 minutes, etc.).

When using exemplary diabetes management system 10, a PWD (or their caregiver) could be responsible for determining when to inject insulin and how much to inject, but system 10 could assist the PWD (or caregiver) in determining an appropriate insulin dose based on current data from the glucose sensor, based on stored therapy parameters, and/or based on data about insulin injections. In some cases, the pen caps can provide data about when the last insulin injection was made by using data from a piston-style detector mechanism provided herein. For example, pen caps 112 and 122 can detect when each pen cap is reapplied to its insulin injection pen using a piston-style detector mechanism provided herein, which can be assumed to be the time of the injection. In some cases, pen caps 112 and 122 can track remaining insulin in an insulin injection pen and determine an amount of each dose. The tracking and amount-determining features are described in U.S. Patent Application Nos. 62/599,963 and 62/648,064, which are all hereby incorporated by reference, and in published patents and application numbers WO 2017/009724 A1; U.S. Pat. No. 8,817,258 B1; and EP 2987 518 B1, which are all hereby incorporated by reference.

Figure 1B:
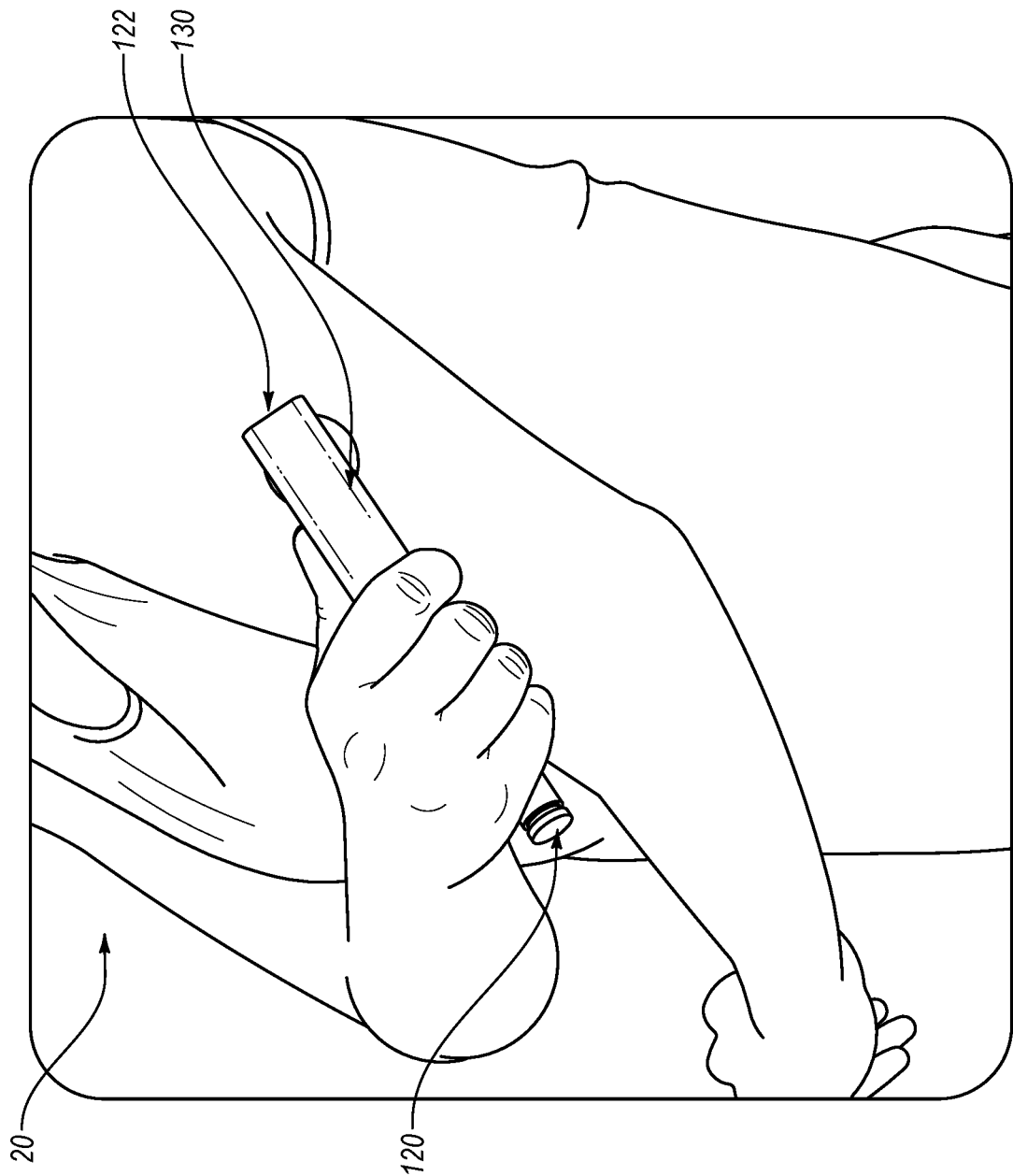
FIG. 1B illustrates how a PWD can have glucose sensor applied to their arm so that it can detect the PWD's blood glucose levels, and how a user could use a pen cap, including an embodiment of a pen cap as described herein, secured to rapid-acting insulin pen to interrogate the glucose sensor.

FIG. 1B illustrates how a PWD 20 can have glucose sensor 130 applied to their arm so that it can detect the PWD's blood glucose levels, and how a user could use pen cap 122, secured to rapid-acting insulin pen 120, to interrogate glucose sensor 130. Before and/or after the user swipes the pen cap 122 in FIG. 1B, pen cap 122 can display therapy relevant information. In some cases, therapy relevant information can include information about one or more recent doses of insulin, glucose data, and/or one or more insulin dose recommendations. For example, pen cap 122 can display a time of the most recent dose before or after it is swiped. In some cases, pen can 122 can display a recommended meal dose of insulin, without a correction component, before pen cap 122 is swiped adjacent to glucose sensor 130. In some cases, pen cap 122 can display a recommended correction dose or recommended meal and correction dose after pen cap 122 is swiped adjacent to glucose sensor 130.

Figure 1C:
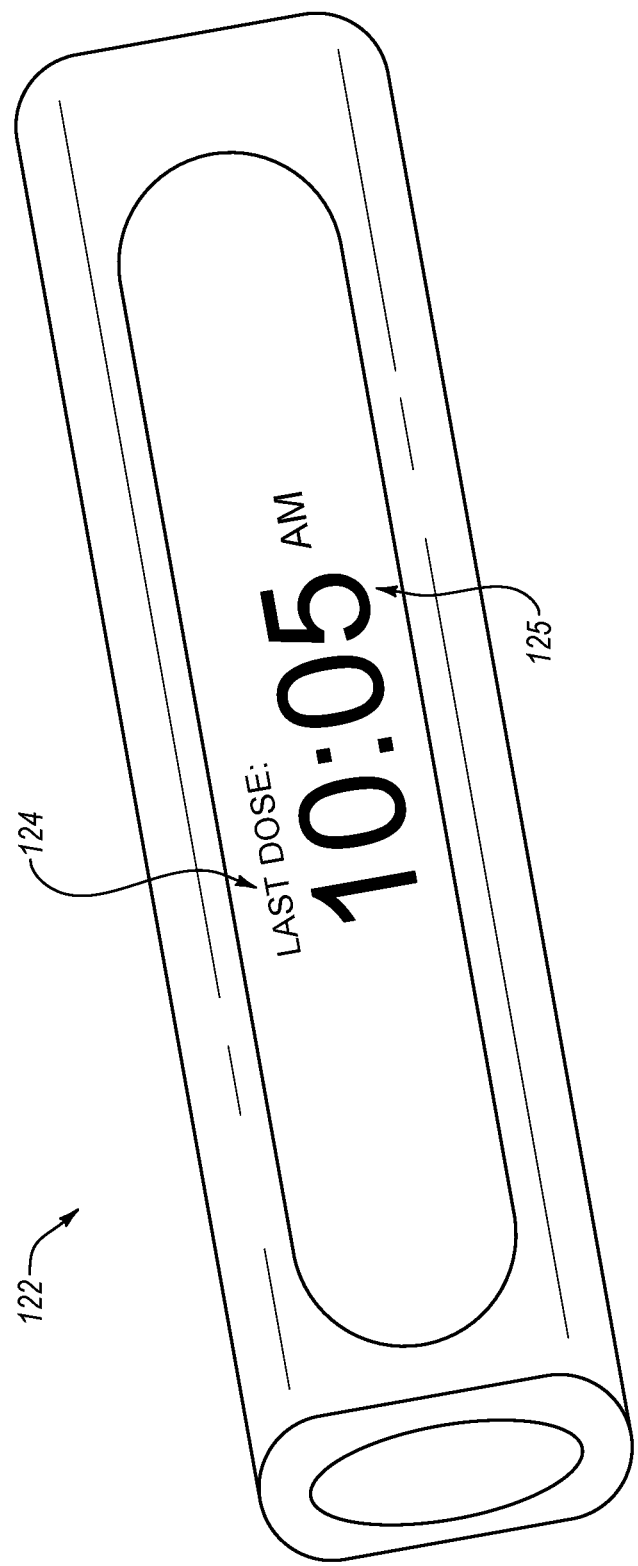
FIGS. 1C-E illustrate information, such as times, recommended dosages, and meal recommendations that can be displayed on the display of a cap of an embodiment, for example, based on a capping or decapping event.

For example, FIG. 1C illustrates a display 124 on pen cap 122 can depict a time 125 of the most recent dose, or "last dose." The time 125 can assist a user in remembering if they have administered a bolus for a recent meal and/or help a user avoid the unintentional stacking of boluses. In some cases, such as cases with pen caps capable of detecting an amount of a dose, the display can additionally display the number of units of the last dose. In some cases, the timing of the last dose could be a clock that ticks up to indicate how long ago the last dose was administered. In some cases, the display might depict a most recently obtained blood glucose level and the time it was obtained. In some cases, the display might be an electronic ink display. In some cases, the display can include identifying information (such as a name of a user, e.g., a label such as "Sarah's pen") and/or information about the type of insulin pen that it is attached to (e.g., the brand of insulin).

Figure 1D:
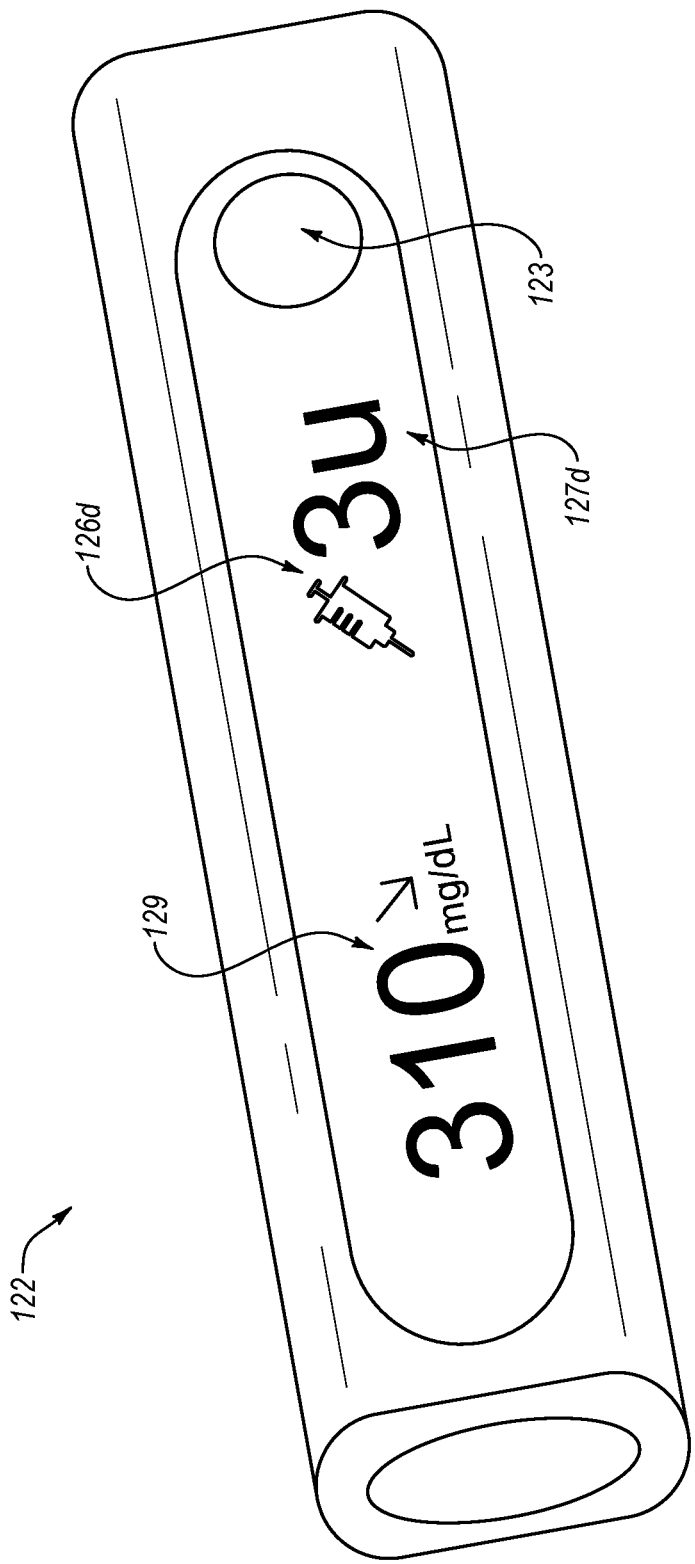

FIG. 1D depicts pen cap 122 showing blood glucose data 129, which can include a current blood glucose level and a trend arrow, which can be received from glucose sensor 130 after capping the pen cap as shown in FIG. 1B. FIG. 1D also includes a recommended correction dose 127d and a corresponding correction dose icon 126d.

Figure 1E:
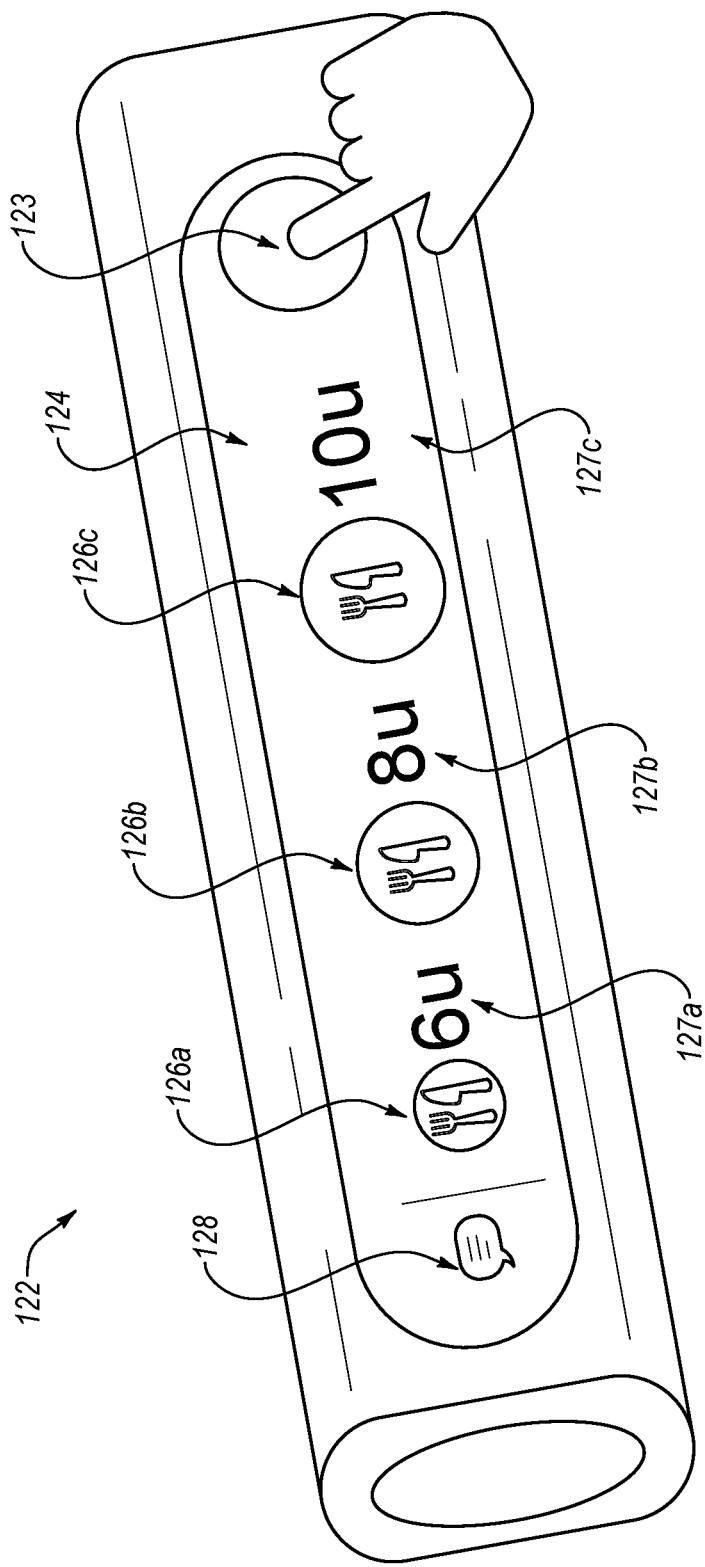

FIG. 1E depicts pen cap 122 with meal recommendations 127a-127c, which can be displayed for differently sized meals that are identified by meal icons 126a-126c. Additionally or alternatively, meal icons 126a-126c can be personalized by the user to represent different types of meals (e.g., B, L, D labels to indicate breakfast, lunch, dinner; or pictures of types of meals such as a salad icon, a sandwich icon, and a pasta icon). For example, in use a user might press button 123 to obtain meal recommendations after seeing the screen of FIG. 1D. In some cases, the meal recommendations can be based on meal doses that are set by a health care professional, the PWD, or a caregiver using the mobile application during set up or as updated by the health care professional, the PWD, or caregiver. In some cases, the meal recommendations can be based on user-specific dosage parameters that are automatically updated by the system, using any suitable algorithm to update dosage parameters. In some cases, when the user has recently (e.g., within the last 5, 10, 15, 20, or 30 minutes) obtained a blood glucose reading, meal recommendations 127a-127c can include both a meal dosage and a correction dosage. In some cases, if pen cap 122 has identified other recent doses (e.g., by detecting a capping action of the pen cap within the last 3 hours, the last 4 hours, or last 5 hours) without knowing the amount of the dose, the pen cap might refuse to add a correction component in order to prevent the unintentional stacking of correction boluses. In some cases, meal icons 126a-126c can indicate whether the recommendation includes a correction component or not. In some cases, additional icons or displays can indicate if there is a recommended correction dose included and/or the size of the recommended correction dose. In some cases, by pushing button 123, the user can obtain a screen that displays the current blood glucose value, trend information (e.g., a trend arrow), and a recommended correction dose. In some cases, if there has been a recent dosage of insulin (e.g., within the last 1, 2, 3, or 4 hours) a warning screen might appear next to or over the recommendation to indicate that there has been a recent dose in order to prevent unintentional stacking of insulin. In some cases, a notice icon 128 can appear on pen cap 122 in order to indicate to the user that a more detailed suggestion, tip, alert, or alarm is available for the user in the mobile application on the mobile device 140.

In an example embodiment, pen cap 112 can be used on a long-acting insulin injection pen 110. As shown in FIGS. 1A-1E, pen caps 112 and 122 can have distinct visual appearances (e.g., different colors) to assist the user to distinguishing between their long-acting insulin and their rapid-acting insulin, as the unintentionally delivery of the wrong type of insulin can cause hypoglycemic or hyperglycemic events. Pen cap 112 can include a button 113 and a display 114. When button 113 is pressed by the user, the display can remind the user about the amount of long-acting insulin 117 (with an appropriate icon 116) that the PWD should inject based on stored therapy parameters. In some cases, if the user has recently uncapped pen cap 112 from pen 110, the display can depict information about when the pen cap 112 was uncapped or other warnings to prevent the unintentional double delivery of long-acting insulin. In some cases, pen cap 112 can provide a notice sound to indicate to a user that it is time to deliver the long-acting insulin based on stored therapy parameters. In some cases, suitable therapy titration algorithms can suggest that a user change the stored therapy parameters and/or automatically update the stored therapy parameters relevant to the dosing of long-acting insulin. In some cases, pen cap 112 can be configured to send a notification to a mobile application to notify the user that it is time to deliver a long-acting insulin dose that has not been taken (e.g., if no long-acting insulin has been dosed in the last 24 hours). In some cases, pen cap 112 can interrogate glucose sensor 130 to receive glucose data and/or receive blood glucose data via the mobile device 140 and/or pen cap 122. In some cases, display 114 can depict recent blood glucose data, the time of that data, and/or glucose trend data (e.g., a trend arrow).

Pen caps 112 and 122 and other methods, devices, and systems provided herein can readily provide a user with therapy relevant information and/or therapy recommendations, and/or can collect and use pen capping information.

Pen caps 112 and 122 can be configured to be in wireless communication with one or more glucose sensors and/or one or more mobile computing devices. In some cases, a pen cap provided herein can be adapted to wirelessly receive glucose data from a glucose sensor and to wirelessly transmit glucose data from the glucose sensor to a mobile computing device. In some cases, a pen cap provided herein can receive glucose data from a glucose sensor using a first wireless communication technique and transmit glucose data to a mobile computing device using a second wireless communication technique. In some case, the first wireless communication technique can have a shorter expected communication range than the second communication technique. In some cases, a user must act to obtain glucose data from the glucose sensor using the first communication technique while the transmission of glucose data via the second communication technique occurs automatically. In some cases, the pen cap uses NFC communications with glucose sensor 130 and the user must bring the pen cap adjacent to glucose sensor 130, which can be subcutaneously placed on the person's body, in order to obtain glucose data. In some cases, the pen cap can use BLE communications with the mobile computing device. BLE communications can be triggered at regular intervals or and/or triggered automatically after glucose data is received by the pen cap from a glucose sensor. In some cases, mobile device 140 can also receive glucose data from a glucose sensor using any suitable technique and glucose data can be transmitted to pen cap 112 or 122 from mobile computing device 140. In some cases, glucose data transmitted from a glucose sensor to a pen cap in a single transmission can include data that can be used by the pen cap to determine at least two Estimated Glucose Values (EGVs) for a time period extending for at least 30 minutes. In some cases, a single transmission can include at least 1 hour of glucose data, at least 2 hours of glucose data, at least 4 hours of glucose data, at least 6 hours or glucose data, or at least 8 hours of glucose data.

Pen caps 112 and 122 can include one or more processors and memory for controlling wireless communications, controlling a user interface, and/or determining therapy recommendations. In some cases, pen caps provided herein can include a processor and associated memory, which can be used with an algorithm to determine a EGVs from raw sensor data. In some cases, a glucose sensor can transmit EGVs. In some cases, pen caps provided herein can include memory that stores user-specific dosage parameters (e.g., recommended daily dose of long-acting insulin or total daily basal dose (TDBD), insulin sensitivity factor (ISF), carbohydrate-to-insulin ratio (CR), total daily insulin dose (TDD), target glucose value, etc.). In some cases user-specific dosage parameters can be time or day dependent, such as CR and ISF values that depend on the hour of the day. In some cases, pen caps provided herein can have memory that stores recommended doses of rapid-acting insulin for different meals or for different meal categories. In some cases, user-specific dosage parameters and/or different recommended doses for different meals can be updated via a mobile computing device in wireless communication with the pen cap. For example, an algorithm in the mobile computing device or in the cloud can update these parameters or recommended doses. In some cases, parameters or recommended doses can be updated by a healthcare professional or manually by the PWD or a caregiver. In some cases, the pen cap can include an algorithm in memory to be executed by the processor to update the user-specific dosage parameters or recommended doses.

Pen caps provided herein can, in some cases, display or otherwise provide notice to a user of a current blood glucose level and/or blood glucose trend data (e.g., a rate of change) based on glucose data received from a continuous glucose monitor, a flash glucose monitor, a blood glucose meter, or any other suitable glucose sensor. Pen caps provided herein can also provide recommended doses of insulin based on one or more of blood glucose data, user-specific dosage parameters, recommended dosage amounts set by a user or healthcare professional, time-of-day, meal data or categorizations, or any other suitable input.

Pen capping information (i.e., information about when the pen cap is secured to and/or released from the injection pen) can include information about a current capping period (e.g., the time since the last capping), information about a duration of one or more uncappings, and the timing (e.g., time-of-day or time elapsed since) of each uncapping and each capping. In some cases, pen capping information can be displayed on the pen cap to a user. In some cases, pen capping information can be announced by a speaker in the pen cap. For example, in some cases, a pen cap can provide a timer clock that counts up from the last time the pen cap was secured to the injection pen. In some cases, a pen cap can wirelessly communicate pen capping information to mobile device 140 (e.g., a smartphone, tablet, etc. running a mobile application).

Pen capping information can be used to adjust the user experience/behavior. In some cases, the pen cap adjusts the presentation of the therapy relevant information and/or recommendations provided to the user based on the pen capping information. For example, in some cases a pen cap may provide bolus recommendations to correct for elevated blood glucose levels based on data from a glucose sensor, but may limit the presentation of such correction bolus recommendations to time periods when the current pen capping duration is greater than a threshold period of time (e.g., at least 3 hours, at least 4 hours, or at least 5 hours). In some cases, the pen cap can provide notifications, alerts, or alarms to the user based on the pen capping information. For example, if the pen cap is removed from the injection pen within a threshold period of time (e.g., within 30 minutes or 1 hour) from a previous capping, the pen cap may provide a visual, audible, or vibrational notification to indicate that the user may have recently used the pen to administer insulin. In some cases, the pen cap can be in wireless communication with a mobile computing device (e.g., a smartphone, tablet) and one or more notifications, alerts, or alarms based on pen capping information can be announced or displayed on the mobile computing device.

Pen capping information can be stored, displayed, and analyzed in combination with glucose data to determine user behaviors, such as whether the person is appropriately dosing insulin for meals and/or to correct elevated blood glucose levels. In some cases, pen capping information can be presented on a graphical representation of blood glucose data for the user and presented to a user and/or to a health care professional. In some cases, blood glucose data from a period of time after each capping event can be evaluated to determine whether the user appropriately dosed insulin for that uncapping event, and whether the user is under-dosed or over-dosed.

Figure 2:
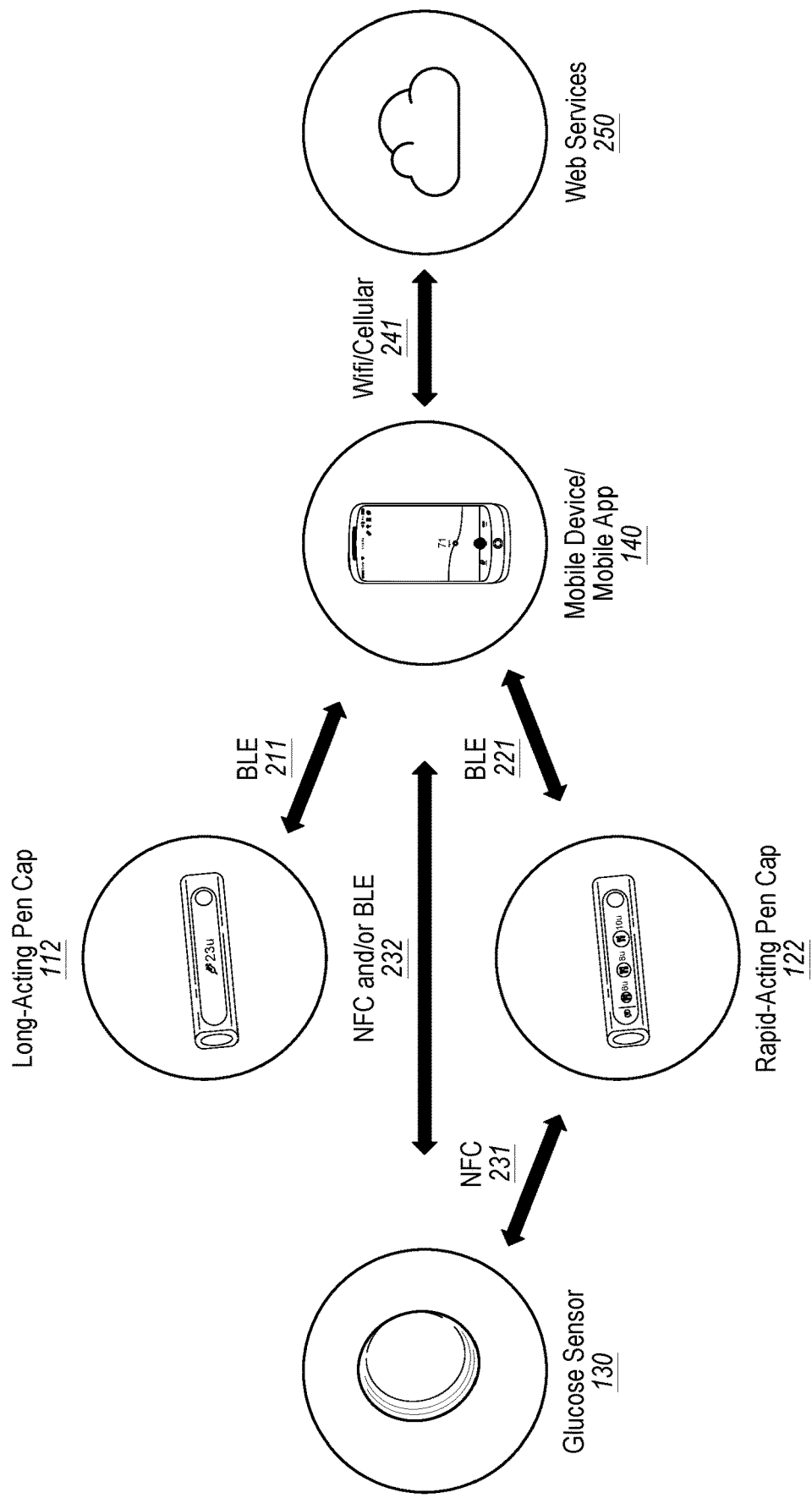
FIG. 2 depicts an exemplary communications architecture for the System depicted in FIG. 1A.

FIG. 2 depicts an exemplary communications architecture for the System depicted in FIG. 1A showing possible communication links between components of the system. The various components can interface with each other via controlled wireless, NFC, or BLE protocols. Each of these components display, transmit, and receive information based on the system workflow in-progress at the specified point in time. As shown, glucose sensor 130 can communicate via NFC with rapid acting pen cap 122, communication link 231, and/or with mobile device 140, communication link 232. In some cases long-acting pen cap 112 can communicate with glucose sensor 130 via NFC communications. In some cases, long-acting pen cap 112 does not directly communicate with the glucose sensor via NFC in order to prevent user confusion because only rapid-acting insulin should be used for a correction or meal dose. In some cases, glucose sensor 130 can additionally communicate with the mobile device via a wireless radio that transmits blood glucose values at predefined intervals. Both pen caps 112 and 122 can communicate with the mobile device 140 via BLE communications. Blood glucose data, programmed therapy parameters (e.g., daily dosage of long-acting insulin, dosages for different meal sizes (which can vary by time of day), insulin sensitivity factor, carbohydrate-to-insulin ratio, etc.), pen capping data (and optionally dose amount data if detected by the pen caps) can be communicated between the mobile device 140 and each pen cap 112 and 122, and system data can be communicated via WiFi or cellular connection 241 to web service 250 (which can be any remote server). In some cases, each pen cap can include a processor and memory configured to run algorithms to determine recommended dosages. In some cases, the mobile device can execute therapy recommendation or therapy parameter update algorithms to recommend changes to programmed therapy parameters and/or to automatically update programmed therapy parameters. In some cases, web services 250 can execute algorithms to recommend changes to programmed therapy parameters and/or to automatically update programmed therapy parameters.

In some cases, initial therapy parameters can be programmed into the mobile application on mobile device 140 and transmitted to the pen caps via BLE communication links 211 and 221. In some cases, pen cap 122 can use therapy parameters received from the mobile app to recommend correction doses and meal doses. In some cases, the therapy parameters can include meal doses for different or differently sized meals (e.g., small meal, medium meal, and large meal or breakfast, lunch, and dinner or salad, sandwich, and pasta). In some cases, the therapy parameters can include a therapy parameter for correcting blood glucose values, such as an insulin sensitivity factor. In some cases pen cap 112 can receive a therapy parameter indicating a daily amount of long-acting insulin. In some cases, pen cap 112 can receive recommended times for dosing long-acting insulin from the mobile device mobile application 140 (e.g., every day at 9 PM, every day at 8 AM, twice a day at 8 AM and 8 PM, etc.).

Pen caps can also be configured to gain insights into which recommended dose the user is likely to be following. For example, as described in U.S. patent application Ser. No. 15/717,805, a pen cap (whether or not there is any dose capture feature incorporated into the pen cap) can include meal announcement categorizations (such as S, M, L), and data from each announcement might indicate whether the user is likely to have dosed an appropriate amount for a S, M, or L meal. U.S. patent application Ser. No. 15/717,805 is hereby incorporated by reference. In some cases, a button on pen cap 122 might be pressed multiple times to show recommendations for successively a S meal, a M meal, and a L meal, and methods and systems provided herein may assume that the user dosed insulin based on the last displayed recommendation. In some cases, information added via the mobile application indicating an amount of insulin left in the pen at various intervals (once a day, once every few days, once a week) can indicate whether the user is generally following the therapy recommendations or whether the user is ignoring them. In some cases, methods and systems provided herein can analyze glucose data, pen capping information, data regarding amounts of insulin left in one or more pens, and/or answers to questions presented via the mobile app to determine a likelihood or rating of the user's conformance to recommended doses. The likelihood or rating can be used by methods and systems provided herein to determine whether to adjust the recommended doses or to provide coaching to the user.

Methods and systems provided herein can additionally include a mobile application that runs on a mobile device (e.g., a smartphone or tablet) that is in wireless communication (e.g., via BLE) with one or more pen caps described herein. In some cases, blood glucose data can be transmitted from the glucose sensor, either via the pen caps and/or directly from the glucose sensor. In some cases, a mobile application can have a user interface that displays a graphical representation of the blood glucose data. In some cases, a graphical display of blood glucose data over time can include indicators communicating pen capping information.

Figure 3A:
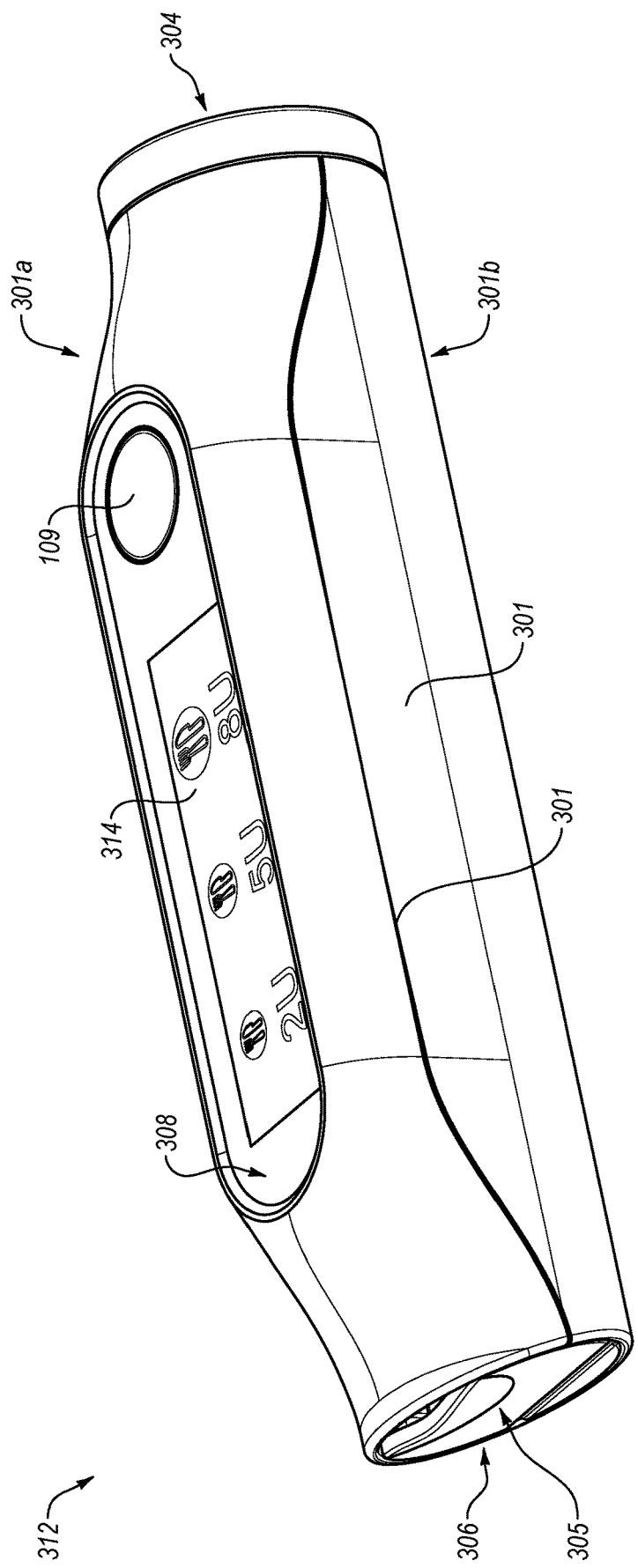
FIGS. 3A-3D are perspective views of a pen cap that includes a piston-style detector mechanism of an embodiment, with close up views of the piston-style detector in FIGS. 3C (top-side view) and 3D (under-side view).
Figure 3B:
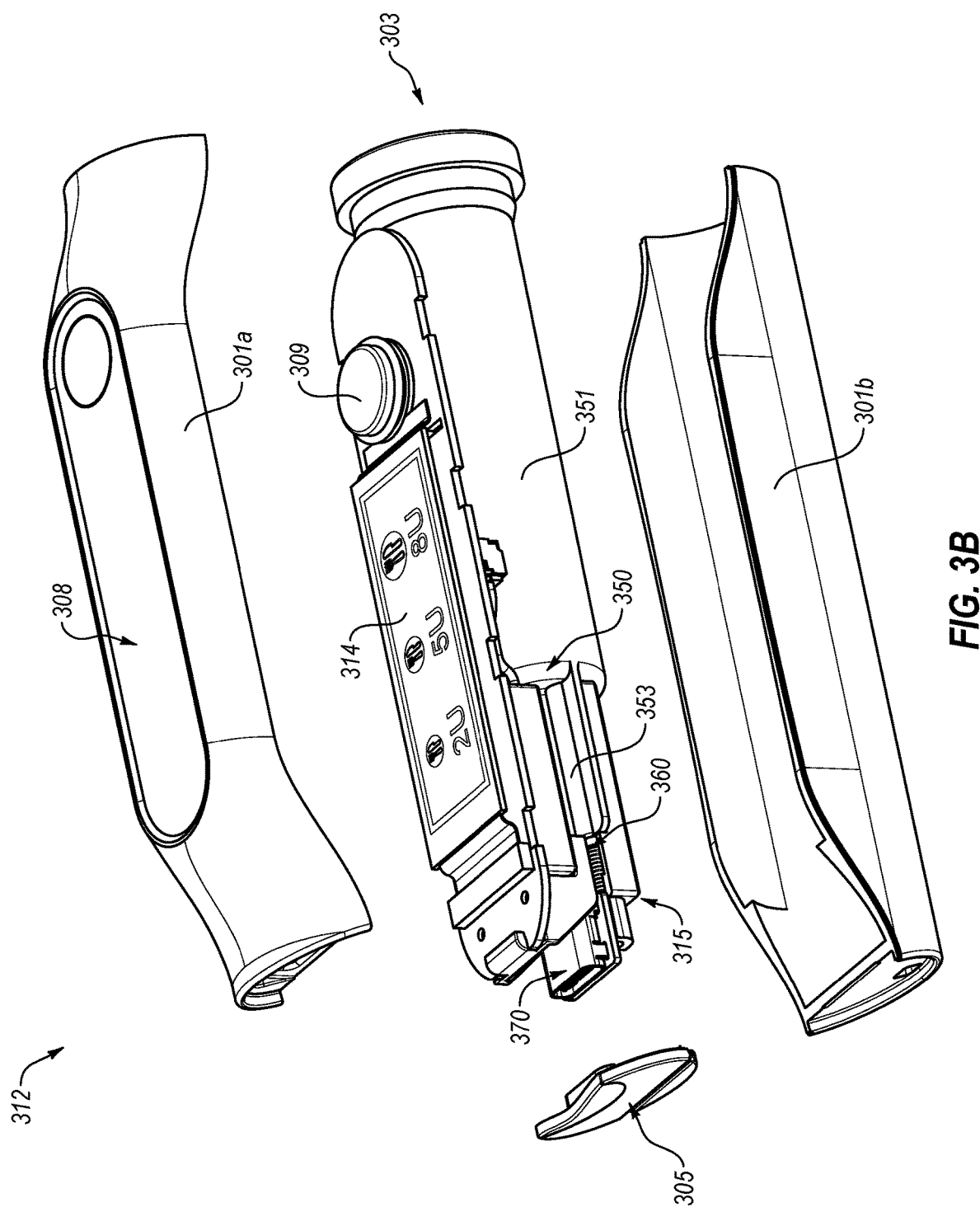

To generate the capping information described above, a mechanism for detecting a capping and/or uncapping event can be incorporated with a pen cap, such as with pen cap 112 and/or pen cap 122. FIGS. 3A-3D illustrate a pen cap 312 for a dosing device, such as a medication delivery pen (not shown). In FIG. 3A, the pen cap 312 is shown as including an outer housing 301 which can accommodate several components therein as shown in FIG. 3B. Outer housing 301 may include a first portion 301a and a second portion 301b connected together at a seam 302 to define a first opening 304 and a second opening 306. First portion 301a and second portion 301b can be connected by friction, snap-fitting, welding, gluing, melting or any other suitable bonding method. In some implementations, outer housing 301 may have a uni-body housing configuration (not shown).

Internal components, such as a display 314 and/or a button 309, can be disposed in outer housing 301. The display, which may be an LCD, e-paper, LED, OLED or any other suitable display, may be viewable through an opening 308 in the outer housing 301. The button 309, which may be a mechanical, spring-loaded button, a touch-responsive button (i.e., a touch screen and/or tactile responsive) may be accessible to a user via the opening 308 or via a separate opening. Outer housing 301, first portion 301a and/or second portion 301b may include one or more of type of plastic, metal, any other suitable material, a combination thereof or any other suitable material(s). The housing may be provided at various degrees of transparency, including from substantially transparent (e.g., internal components can be seen through the housing) to substantially opaque (e.g., internal cannot be seen through the housing). The housing may be manufactured by any suitable process for manipulating the materials from which they may be made, for example, machining (e.g., CNC, lathe, etc.), additive manufacturing (e.g., 3D printing), injection molding, blow molding, casting, punching, laser-cutting, etc.

As illustrated in the exploded view of the pen cap 312 shown in FIG. 3B, along with the display and button, a piston-style detector mechanism 315 is disposed in outer housing 301. The display, button and piston-style detector mechanism 315 can be attached together, for example, to form a common unit. The common unit can have a modular design with each component separately attachable/removable to/from the others. For example, the display 314, the button 309, and piston-style detector mechanism 315 may be mountable via, for example, on a common support base (not visible) and may be connectable to a circuit board (not visible) along with a memory and a processor that is in communication with the memory and configured to execute instructions stored in the memory; and an on-board power source (not shown) such as a rechargeable battery.

Piston-style detector mechanism 315 includes an inner shell 350 designed to receive an insulin delivery pen, a piston assembly 360 configured to interact with a pen as it is secured to the pen cap (capping event) or removed from the pen cap (uncapping event), and an electronic circuit 370 configured to provide an electrical pathway for communicating the capping or uncapping event from the piston assembly to the circuit board, and eventually the processor. For example, the electronic circuit 370 transmits a signal when the piston assembly 360 interacts with the pen during the capping or uncapping of a medication delivery pen via opening 303.

Inner shell 350 includes a pen body-securing portion 351, a needle-securing portion 353, and an opening 303 through which a pen can be inserted into a pen-receiving cavity (not visible) and a passageway (not visible) to provide the piston assembly 360 access into the cap as shown in FIGS. 3C-3E, 4A-4B and 5A-5D and further described below.

Figure 3C:
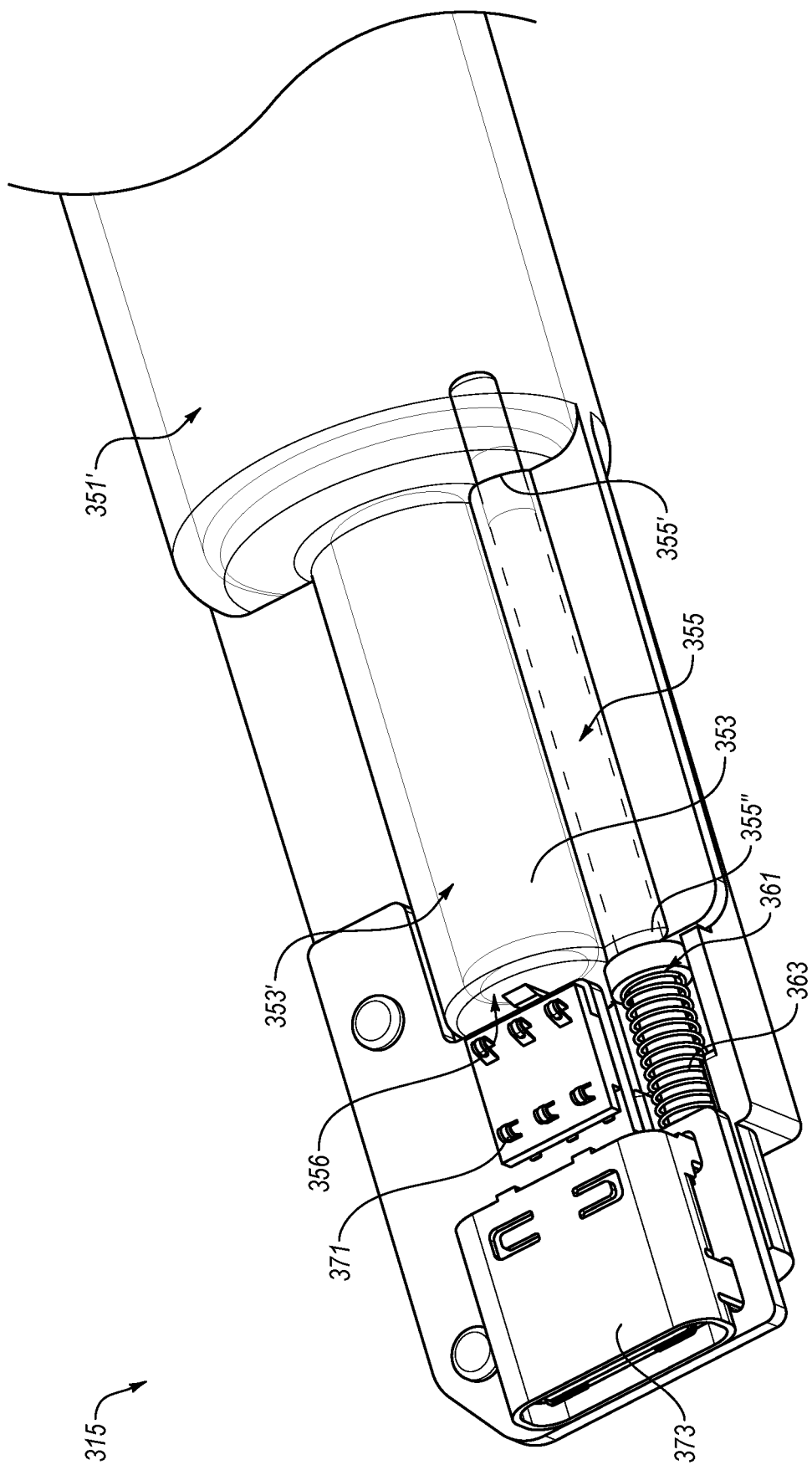
Figure 3D:
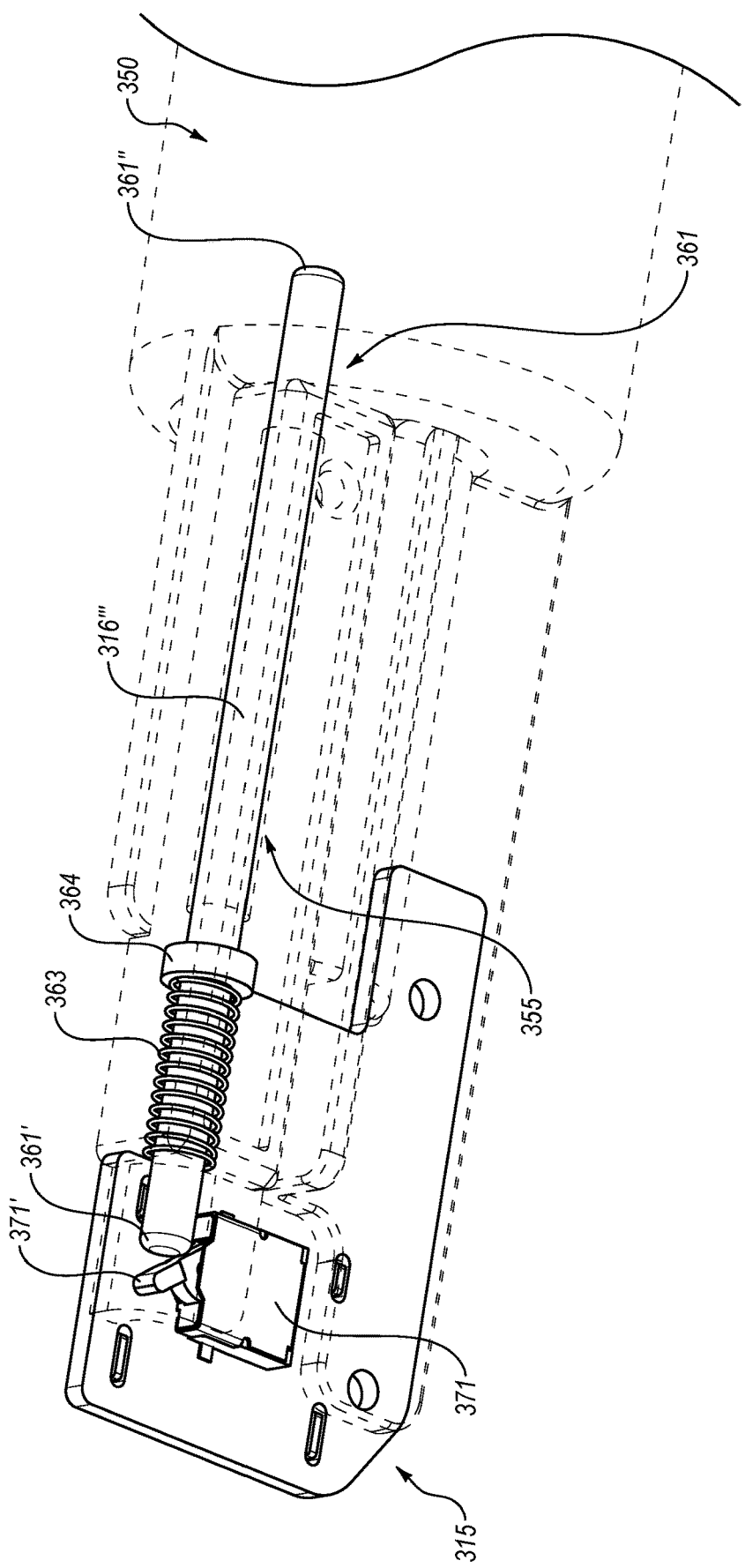
Figure 3E:
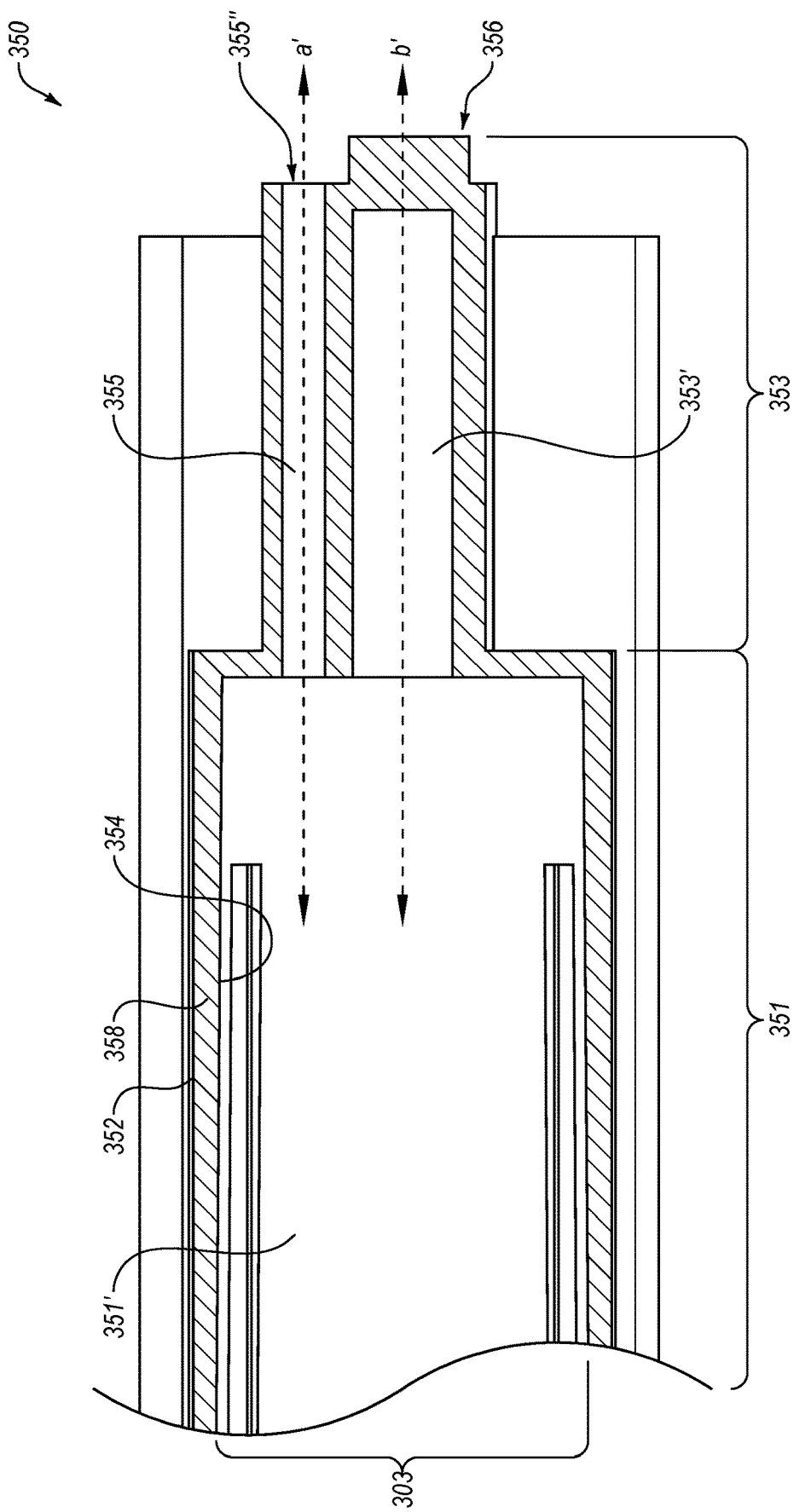
FIG. 3E is a cross-sectional view of the inner shell of the pen cap of FIGS. 3A-3D.

As illustrated in the zoomed in views in FIGS. 3C-3E, the inner shell 350 of the piston-style detector mechanism 315 can further include a second end 356 opposite the first end 303, and a sidewall 358 defined by an outer surface 352 and an opposing inner surface 354. The sidewall 358 extends between the first end 303 and the second end 356 to define a pen-receiving cavity 351'. The second end 356 can further define a needle-accepting cavity 353'. The passageway 355 includes a first opening 355' adjacent to cavity 351' and a second, opposing opening 355". The passageway 355 allows the translatable shaft 361 to be slideably disposed through at least a portion of the inner shell 350.

For example, the electronic circuit 370 includes, at least one switch 371 that can be manipulated by a piston assembly 360, such as in response to receiving a medication delivery pen 380 in opening 303. The at least one switch can be a microswitch having a toggle arm 371'. In some implementations, the at least one switch can be a "normally-open" switch such that when incorporated in a circuit, without an external influence to toggle the switch, it defaults to an open circuit configuration. In some implementations, the at least one switch can be a "normally-closed" switch such that when incorporated in a circuit, without an external influence to toggle the switch, it defaults to an open circuit configuration.

The piston assembly 360 includes a translatable shaft 361 that can be at least partially disposed in the passageway 355. The translatable shaft 361 can include a body that extends at least from a pen-interfacing portion 361" to a switch-interfacing portion 361' thereof. As described further below and shown in more detail in FIGS. 4A-4B and 5A-5B, the translatable shaft 361 is oriented to travel from a first location to at least a second location during capping of the medical delivery pen with the pen cap to toggle the at least one switch. Upon removing the pen, the translatable shaft 361 can be configured to return to the first location. For example, a piston return 363 can be configured to automatically cause the translatable shaft 361 to return to the first position.

Figure 4A:
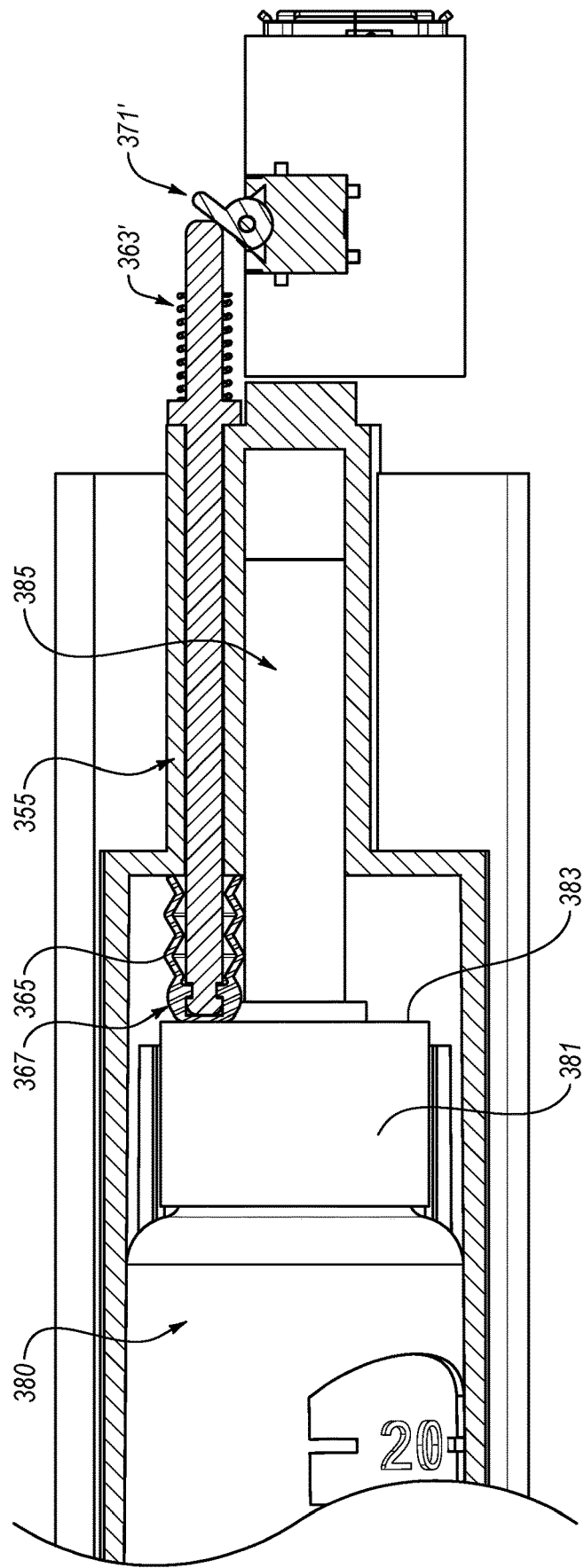
FIGS. 4A-4B are cross-sectional views showing operation of a piston-style detector mechanism when a medication delivery pen with needle attached thereto is inserted into a pen cap of an embodiment.
Figure 4B:
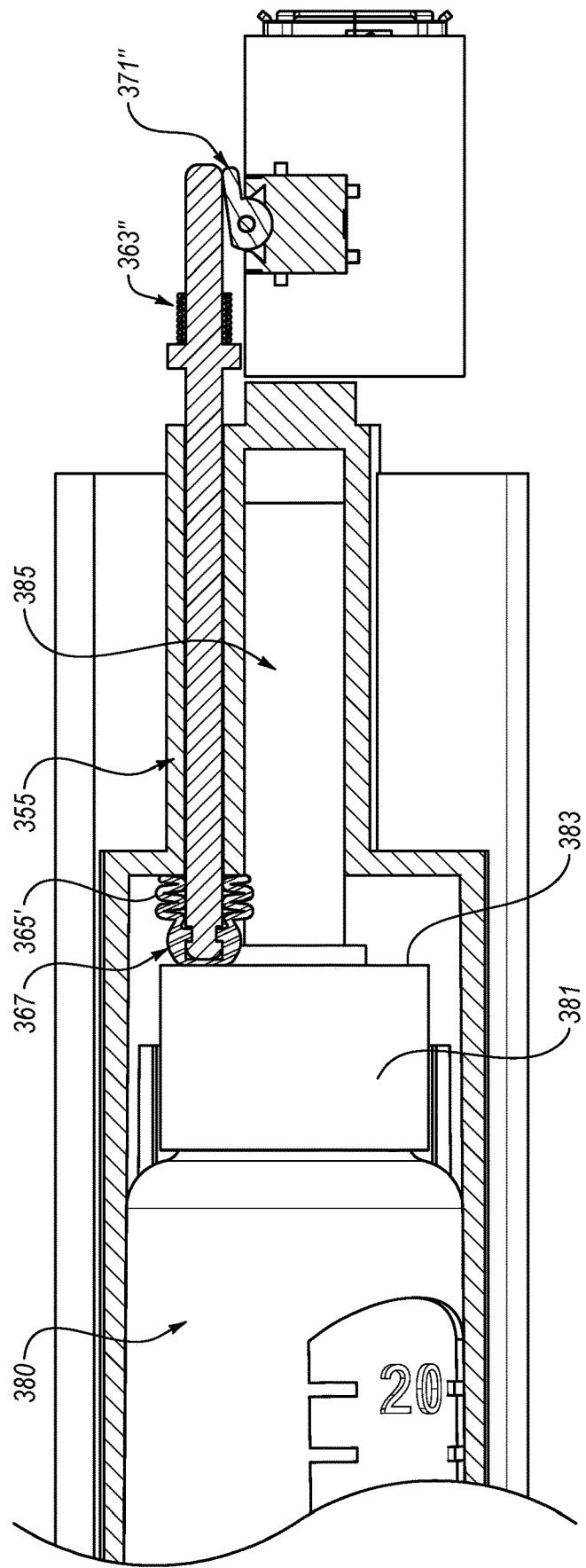
Figure 5A:
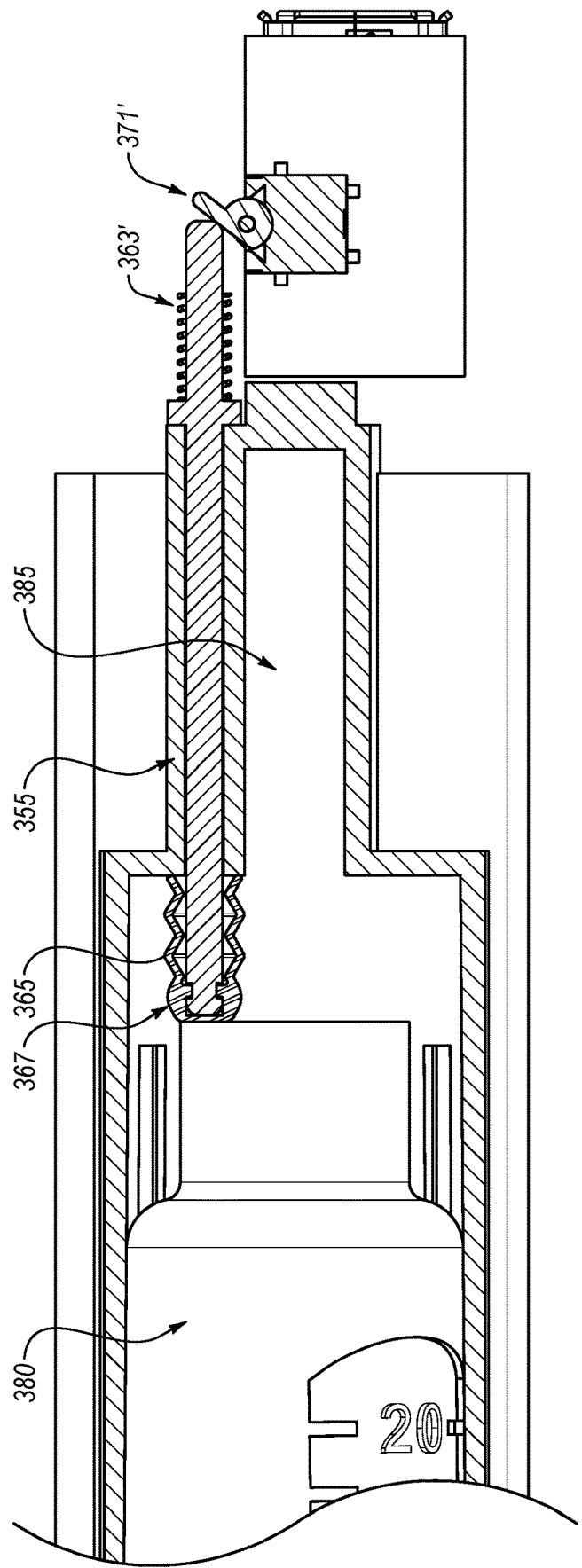
FIGS. 5A-5B are cross-sectional views showing operation of a piston-style detector mechanism when a medication delivery pen without a needle attached thereto is inserted into a pen cap of an embodiment.
Figure 5B:
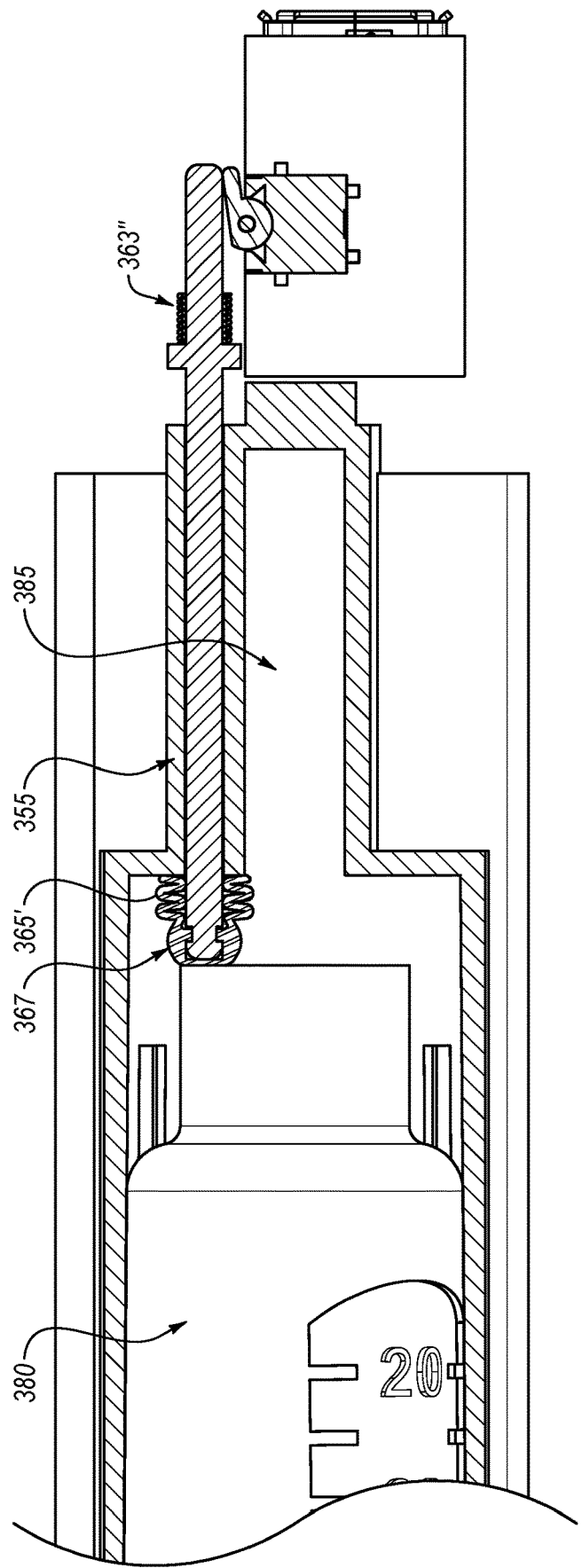

FIGS. 4A-4B are cross-sectional views showing operation of the piston-style detector mechanism when a medication delivery pen with needle attached thereto is inserted into a pen cap of an embodiment. As described above, translatable shaft 361 can be slidably disposed in the passageway 355 via first opening 355' and second opening 355". During capping or uncapping of the medical delivery pen with the pen cap, the translatable shaft is oriented to travel from a first location to at least a second location as illustrated between FIGS. 4A and 4B and between FIGS. 5A and 5B. As illustrated, the piston return 363 can include a spring that is disposed concentrically with the shaft and disposed between the second opening 355" and the switch-interfacing portion 361'. To prevent the translatable shaft 361 from sliding completely through the passageway 355 and into the pen-receiving cavity 351', it can include a limiter 364, for example a collar component or an integrated shoulder portion which has a wider diameter than second opening 355" of the passageway 355.

Additionally, outer housing 301 mates with the inner shell 350 of the piston-style detector mechanism 315 to define at least an inner cavity and in a manner to prevent the ingress of moisture or any other foreign material that could harmful to some components of the piston-style detector mechanism, such as circuit 370 and the at least one switch 371 which can separately or together be positioned within the inner cavity, for example, between the inner shell 350 and the outer housing 301. The outer housing 301 and inner shell 350 may mate such as to provide protection from liquid ingress into the inner cavity and can, therefore, form a water-tight inner cavity, or a cavity having a level of water-resistance of IPX5 or better (IEC Standard 60529). To prevent ingress of moisture or any other foreign material that may enter the inner cavity from the pen-receiving cavity 351', a seal 365 can be disposed at the second opening 355". The seal may be a boot seal which can become compressed between the first opening 365' and the pen 380. The seal may instead be or further include a coating, for example, a sealant and/or lubricant composition coated on a surface of the piston's body.

In an embodiment, switch 371 can detect one, two, three or different configurations. For example, toggle 371' can be toggled to two different positions (e.g., a first position and a second position) or three different positions (first, second and third). For example, toggle 371' can be in a first "open" toggle position in which pen cap and pen are not secured to one another, and therefore the translatable shaft to is in its home, undisturbed location; and a second toggle position in which the pen cap is secured to an injection pen that does not include a needle attached and the piston is caused to travel a first distance. Toggle 371' can additionally be in a third toggle position in which the pen cap is secured to an injection pen that has a needle attached and the piston is caused to travel a second distance that may be the first or second distance depending on the configuration of the pen.

The shape, size and orientation of the piston can also be relied on for providing various contact to a foreign object, like a pen, being inserted into the pen cap. For example, in some cases, the piston can include a first section having a first outer diameter and a second section having a second outer diameter so that the piston moves the switch to the third toggle configuration if the needle is secured but only moves to the second configuration if the needle is not secured. In another example, the piston can have a diameter that gradually reduces from a first location to a second location along the length of the piston's body so that the switch can determine the relative depth of the pen inserted into the pen cap and thus that data to determine if a needle is attached to the pen. Data about whether the needle is attached to the pen can be used to determine if a user is likely changing the needle between each injection or keeping a needle on the pen for multiple injections. In some cases, data about the needle being attached to the pen can be used to determine a resupply quantity of needles to the user and/or to provide instructions to the user about the proper changing of needles. In an embodiment, the switch can include a proximity sensor to detect a distance traveled by the translatable shaft, for example, to assess how far a medication delivery pen has been inserted into the inner-shell of the pen cap or whether the pen has been fully inserted (i.e., secured) in the inner shell of the pen cap.

In an embodiment, the passageway for the translatable shaft is configured parallel to a long-axis of the inner shell. In an embodiment, the passageway 355 for the translatable shaft 361 is configured offset from and parallel to a long-axis of the inner shell. In an embodiment, the translatable shaft is disposed offset from and travels in a direction (a-a') parallel to a central axis (b-b') of the inner shell 350. Accordingly, the detection of the capping or uncapping event can be made not subject to the presence or nonpresence of a needle on the pen. This is because an interface location 383 between the pen with the piston-style detection mechanism is at the pen-body shoulder 381.

Like pen caps 112 and 122 as described above and illustrated in FIG. 1A-1E, the pen cap 312 may be included as part of a system that further includes an analyte sensor system (e.g., blood-glucose meter, a flash glucose monitor, or a continuous glucose monitor) in communication with the pen cap and/or a mobile-computing device that can be used to configure therapy parameters, including one or more of recommended doses for differently sized meals, insulin sensitivity factors, carbohydrate-to-insulin ratios, daily dose of long acting insulin or combinations thereof. The cap can be in wireless communication with the mobile-computing device so as to, for example, transmit dose-timing data to a remote user interface. The wireless communication can include pairing the pen cap to the analyte sensor system, setting or updating therapy parameters and sending therapy information. The wireless communication can include sending therapy information to a cloud for one or more analyses, updating therapy parameters, or a combination thereof. The wireless communication also includes information such as capping-event data, analyte data or a combination thereof.

Pen caps can include an NFC reader adapted to obtain blood glucose data from the glucose sensor when brought within an interrogation distance of the glucose sensor. With a glucose sensor applied to their arm to detect a PWD's blood glucose levels, the PWD can swipe such a pen cap secured to a rapid-acting insulin pen within an interrogation distance of the glucose sensor in order to initiate the interrogation of the glucose sensor.

Figure 6A:
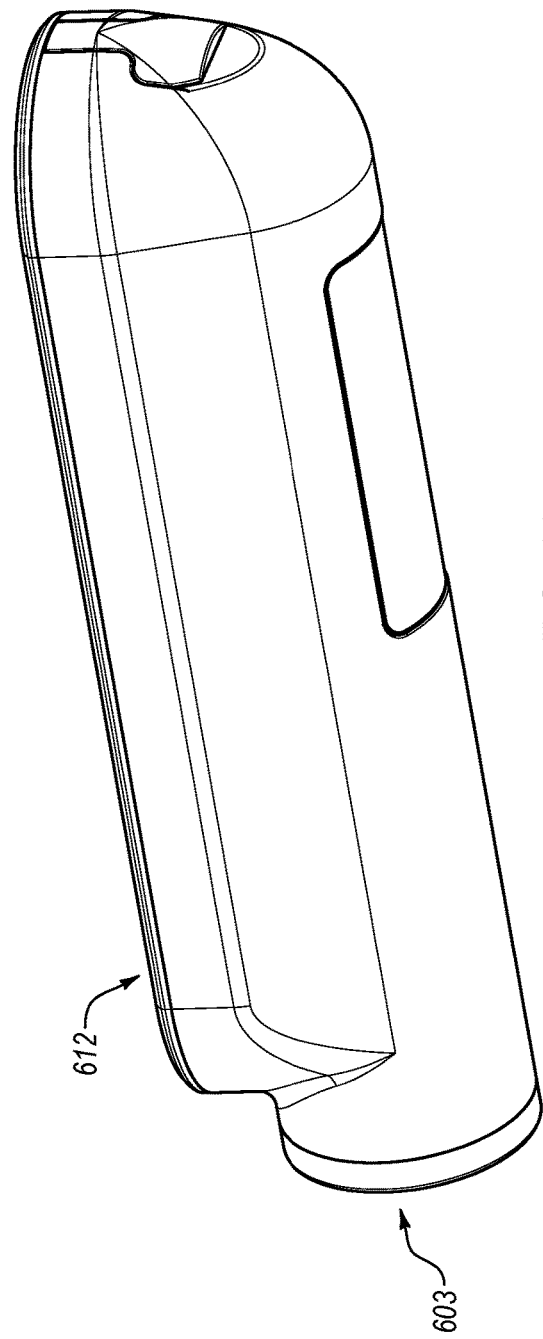
FIGS. 6A-6C are perspective views of different levels of detail of a pen cap that includes at least two NFC antennas according to an embodiment.
Figure 6B:
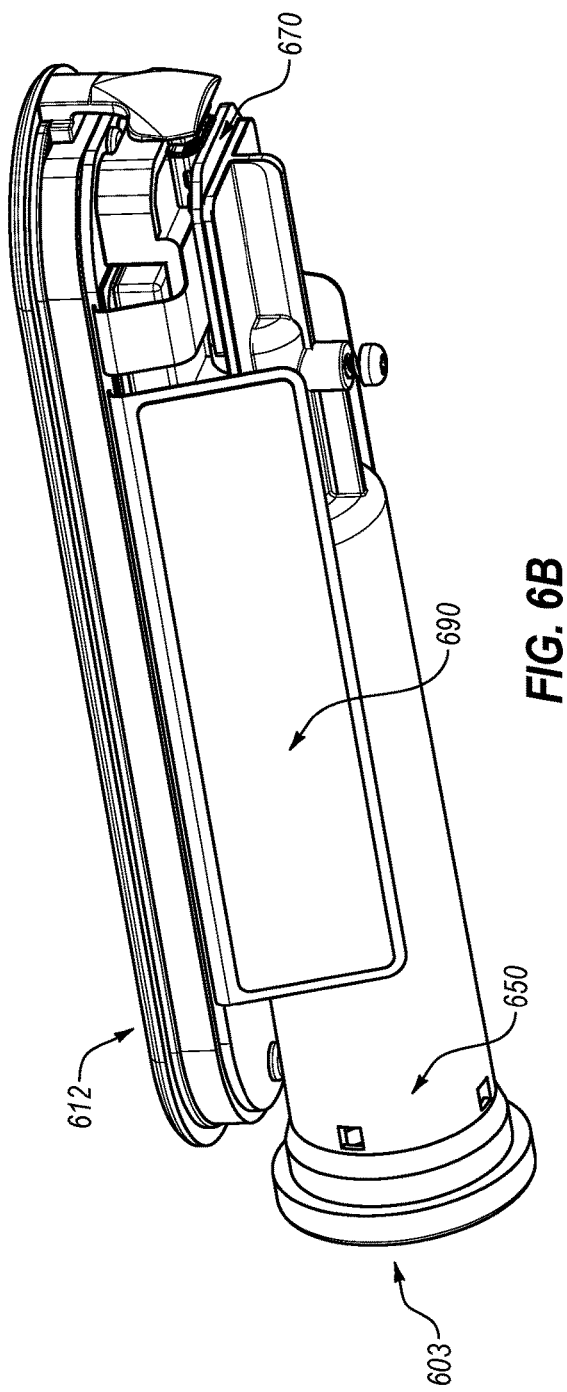
Figure 6C:
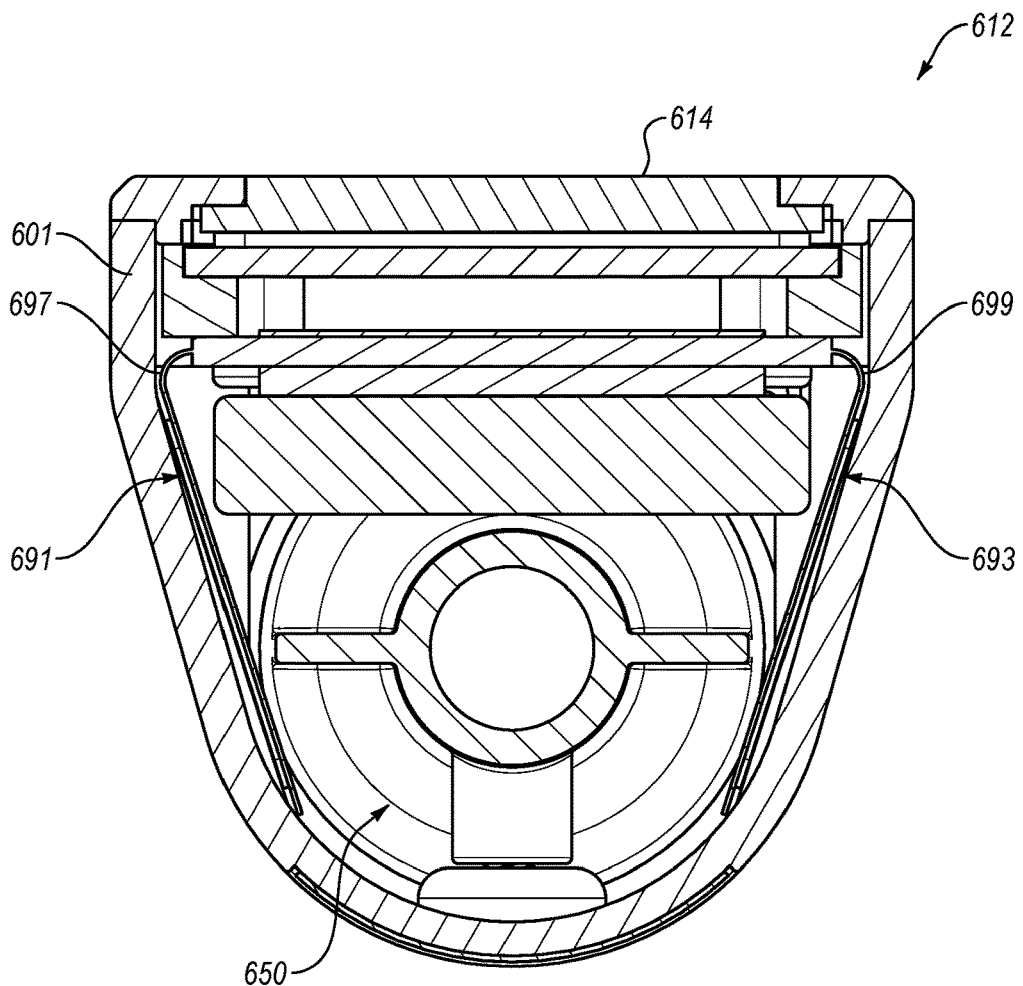

FIGS. 6A-6C illustrate perspective views of a pen cap 612 for a dosing device such as a medication delivery pen (not shown). As illustrated, the pen cap 612 includes outer housing 601; a display 614; and an inner shell 650 that mates with the outer housing 601. The inner shell 650 can include a first open end 603 through which a pen can be inserted, a second end 656 opposite the first end 603, and a sidewall defined by an outer surface and an opposing inner surface, with the sidewall extending between the first end (opening 603) and the second end, thereby defining a pen-receiving cavity (not visible). A first NFC antenna 691 can be configured to receive at least one signal generated by a transcutaneous sensor. The first NFC antenna 691 can be positioned between the housing and a first side of the inner shell 650. Meanwhile, a second NFC antenna 693 can be configured to receive the at least one signal generated by a transcutaneous sensor and positioned between the outer housing 601 and a second side of the inner shell 650. In an example, the inner shell 650 is disposed between the first NFC antenna 691 and the second NFC antenna 693.

The pen cap 612 for a medication delivery pen as described herein may also include a memory (not visible); a processor in communication with the memory (not visible) configured to execute instructions stored in the memory; and an NFC reader (not visible) in communication with the processor.

Like pen caps 112 and 122 as described above and illustrated in FIG. 1A-1E, the pen cap 612 may be included as part of a system that further includes an analyte sensor system (e.g., blood-glucose meter, a flash glucose monitor, or a continuous glucose monitor) in communication with the pen cap and/or a mobile-computing device that can be used to configure therapy parameters, including one or more of recommended doses for differently sized meals, insulin sensitivity factors, carbohydrate-to-insulin ratios, daily dose of long acting insulin or combinations thereof. The cap can be in wireless communication with the mobile-computing device so as to, for example, transmit dose-timing data to a remote user interface. The wireless communication can include pairing the pen cap to the analyte sensor system, setting or updating therapy parameters and sending therapy information. The wireless communication can include sending therapy information to a cloud for one or more analyses, updating therapy parameters or a combination thereof. The wireless communication also includes information such as capping-event data, analyte data or a combination thereof.

Figure 6D:
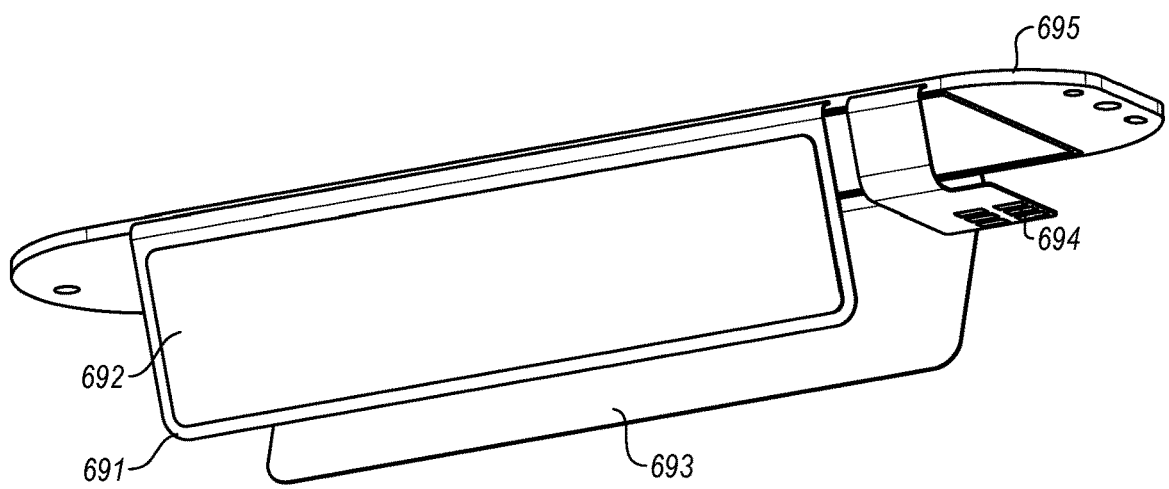
FIG. 6D is a perspective view of a dual NFC antenna that may be incorporated for use in the pen cap of FIGS. 6A-6C.

As illustrated in FIGS. 6C-6D, an antenna for use in cap 612 includes the first NFC antenna 691 and the second NFC antenna 693 disposed on a common substrate and separated by a base portion 695. The substrate includes the base portion 695, a first substrate portion on which the first NFC antenna 691 is disposed and a second substrate portion on which the second NFC antenna 693 is disposed. The first NFC antenna 691 is separated from the base portion by a first bent or hinged portion 697. The second NFC antenna 693 is separated from the base portion by a second bent or hinged portion 699. The antenna may be connected to the circuit 670 by way of contact 694. Stiffeners like that shown at 692 can be added to the antenna to prevent damage to the antennae. The first NFC antenna 691 and the second NFC antenna 693 may be disposed on opposing sides of display 614. For example, first NFC antenna 691 may be disposed on a first side of display 614 and second antenna 693 may be disposed on an opposing, second side of display 614. The first NFC antenna 691 and the second NFC antenna 693 may be oriented substantially perpendicular to a main display surface of the display 614. For example, first NFC antenna 691 and the second NFC antenna 693 may each or separately be oriented between substantially parallel to display 614 to substantially perpendicular to display 614, such as at an angle of from about 0° to about 90°, such as from about 15° to about 85° and even from about 35° to about 65° including at about 45° relative to the main display surface of display 614.

It is noted that features of the cap 312 as described above can be combined with features of cap 612. For example, a cap for a dosage device such as a medication delivery pen can include both a piston-style detector mechanism for detecting insertion/removal of a pen and a dual antenna system such as that described with the first and second NFC antennas. Accordingly, inner shell 650 can include any and all features of inner shell 350.

Figure 7B:
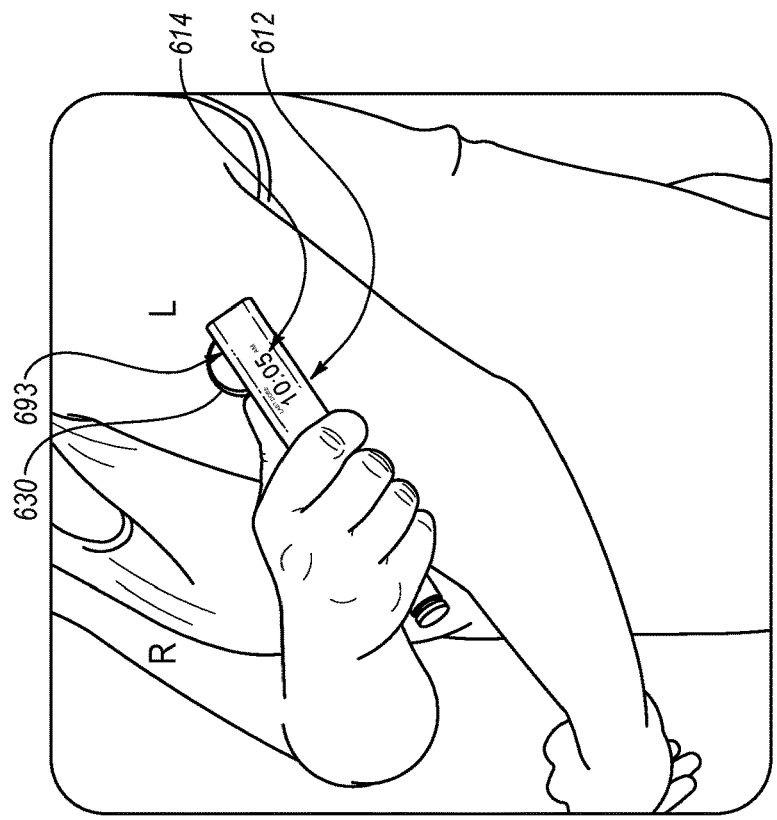
FIGS. 7A-7B illustrates how a PWD can have glucose sensor applied to their right arm (FIG. 7A) or their left arm (FIG. B) so that it can detect the PWD's blood glucose levels, and how a user could use the pen cap of FIGS. 6A-6C secured to rapid-acting insulin pen to interrogate the glucose sensor on either arm.
Figure 7A:
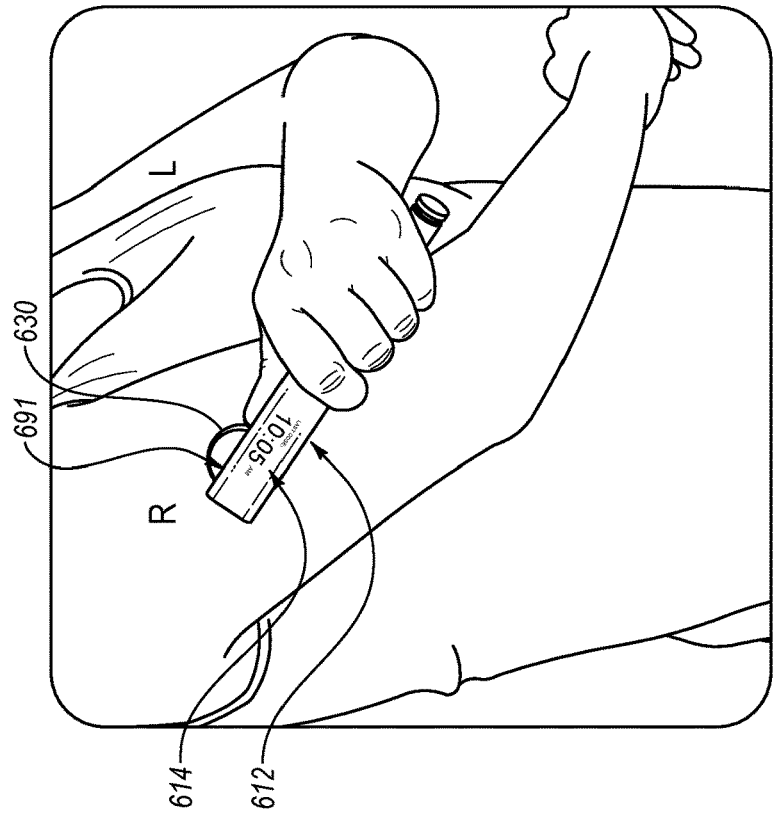

FIGS. 7A-7B illustrate methods for detecting signals generated by a sensor, such as an analyte sensor which may be disposed as a subcutaneous sensor. Specifically, the method describes how a PWD can have glucose sensor applied to their right arm (FIG. 7A) or their left arm (FIG. 7B) so that it can detect the PWD's blood glucose levels, and how a user could use the pen cap of FIGS. 6A-6C secured to rapid-acting insulin pen to interrogate the glucose sensor on either arm.

The pen cap 612 that includes first NFC antenna 691 and second NFC antenna 693 is placed adjacent to an analyte sensor 631. As shown in FIG. 7A, in some implementations during the placing of the pen cap adjacent to the analyte sensor 630 that can be subcutaneously placed in the right arm, the first antenna 691 is closer to the subcutaneous sensor than is the second antenna 693. In an example, as shown in FIG. 7B, in some implementations during the placing of the pen cap adjacent to the analyte sensor 630 that can be subcutaneously placed in the right arm, the second NFC antenna 693 is closer to the subcutaneous sensor than is the first NFC antenna 691. An NFC reader can be activated to alternate reading between first NFC antenna 691 and second NFC antenna 693. With reference to FIGS. 6A-6C, the first NFC antenna 691 and the second NFC antenna 693 can be positioned between the outer housing 601 and the inner shell 350 such that when the pen cap 612 is oriented in, for example, a first orientation, relative to an analyte sensor 630 (e.g., as in FIG. 7A), a signal strength of at least one signal, for example, as generated by the analyte sensor, is received at a higher magnitude of strength by the first NFC antenna 691 than by the second NFC antenna 693. And, when the pen cap 612 is oriented in a second orientation, for example, relative to the analyte sensor 630 (e.g., as in FIG. 7B), the signal strength of the at least one signal is received at a higher magnitude of strength by the second NFC antenna 693 than by the first NFC antenna 691.

Pen cap 612 can be held in a manner such that it has a first orientation when a user is holding the device while scanning for a glucose sensor 630 that is applied on their right arm "R" as shown in FIG. 7A. Alternatively, pen cap 612 is held in a manner such that it has a second orientation when the user is scanning for the glucose sensor 630 that is applied on their left arm "L" as shown in FIG. 7B. In some implementations, the displayed information provided by display 614 may auto-rotate. This would allow the user to read the information "right side up" without having to be inconvenienced by text presented "upside-down" by a display without auto-rotate functionality. The orientation of the displayed information, therefore, would help the user quickly identify whether the sensor is on the left or right arm.

The instruction to pick a display orientation based on a stored orientation during last scan side, for example, until the glucose sensor is scanned on the opposite sides could be an instruction stored in the memory and executed by the processor. The instruction could be executed based on user input or based on a sensed condition, such as a change in a direction of gravity as sensed by an on-board accelerometer. Alternatively, the information provided by display 614 may not auto-rotate, thereby remaining static regardless of the housing's orientation or which arm is being scanned.

While the embodiments have been illustrated with respect to one or more implementations, alterations and/or modifications can be made to the illustrated examples without departing from the spirit and scope of the appended claims. In addition, while a particular feature of the embodiments may have been disclosed with respect to only one of several implementations, such feature may be combined with one or more other features of the other implementations as may be desired and advantageous for any given or particular function.

Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments will be apparent to those skilled in the art from consideration of the specification and practice of the descriptions disclosed herein. It is intended that the specification and examples be considered as exemplary only, with a true scope and spirit of the embodiments being indicated by the following claims.

What is claimed is:

1. A pen cap for a medication delivery pen, comprising:
   a detector mechanism including:
      an inner shell, including:
         a first open end configured to receive a medication delivery pen,
         a second end, and
         a sidewall defined by an outer surface and an opposing inner surface, the sidewall extending between the first open end and the second end, the sidewall at least partially defining a pen-receiving cavity, and
      a passageway that extends through the inner shell;
   at least one switch; and
   a translatable shaft at least partially disposed in the passageway and including a body that extends at least from a pen-interfacing portion in the pen-receiving cavity to a switch-interfacing portion thereof, wherein the translatable shaft is oriented to travel from a first location to at least a second location during capping of a medical delivery pen into the inner shell to toggle the at least one switch,
   wherein the translatable shaft is offset from and travels in a direction parallel to a central axis of the inner shell.

2. The pen cap of claim 1, further comprising an outer housing, wherein the outer housing mates with the inner shell to define at least an inner cavity, wherein the at least one switch is positioned within the inner cavity between the inner shell and the outer housing.

3. The pen cap of claim 2, further comprising:
   a processor in communication with the at least one switch in the inner cavity;
   memory in communication with the processor in the inner cavity;
   a wireless communication means in the inner cavity; and
   a display,
   wherein the processor is configured to execute instructions stored in the memory, and
   wherein the instructions include:
      maintaining a time, wherein the time is one or more of an actual time of day, a time of day of a most recent toggling of the at least one switch, an amount of time since the most recent toggling of the at least one switch, a time representative of a timing of a recent dosage from the pen, or a combination thereof;
      recording the time; and/or
      displaying one or more of the recorded time; a blood glucose data from a glucose sensor system, recommended doses based on therapy parameters stored in the memory, or a combination thereof.

4. The pen cap of claim 2, wherein the inner cavity is at least water-resistant.

5. The pen cap of claim 1, wherein the second end of the inner shell defines a needle-accepting cavity.

6. The pen cap of claim 1, further comprising a limiter that restricts the travel of the translatable shaft.

7. The pen cap of claim 1, further comprising a spring formed concentric with the translatable shaft and disposed between the first open end and the switch-interfacing portion.

8. The pen of claim 1, further comprising a spring, wherein the spring is oriented such that the spring attains a compressed state during capping of the pen, and wherein the spring is oriented such that the spring returns to at least a less compressed state during uncapping of the pen from the pen cap.

9. The pen cap of claim 1, wherein the at least one switch is a normally open-type switch.

10. The pen cap of claim 1, further comprising a seal, and/or
wherein the seal includes a boot seal extending around a portion of the translatable shaft extending into the pen-receiving cavity, and/or
wherein the seal includes a hydrophobic lubricant in the passageway along the translatable shaft.

11. The pen cap of claim 1, wherein the at least one switch includes one or more of a mechanical switch, an optical switch, a magnetic switch or combinations thereof.

12. The pen cap of claim 1, further comprising a proximity sensor, wherein the proximity sensor is configured to sense a travel distance of the translatable shaft.

13. A method for detecting capping of a medication delivery pen, the method comprising:
receiving a medication delivery pen by a pen cap, wherein the pen cap includes:
a detector mechanism including:
an inner shell, including:
a first open end configured to receive a medication delivery pen,
a second end, and
a sidewall defined by an outer surface and an opposing inner surface, the sidewall extending between the first open end and the second end, the sidewall at least partially defining a pen-receiving cavity, and
a passageway that extends through the inner shell;
at least one switch; and
a translatable shaft at least partially disposed in the passageway and including a body that extends at least from a pen-interfacing portion in the pen-receiving cavity to a switch-interfacing portion thereof, wherein the translatable shaft is oriented to travel from a first location to at least a second location during capping of a medical delivery pen into the inner shell to toggle the at least one switch; and
communicating a motion of the medication delivery pen to the translatable shaft during the capping so that the switch-interfacing portion is configured to cause the toggling of the at least one switch when the switch-interfacing portion interfaces with the at least one switch,
wherein the translatable shaft is offset from and travels in a direction parallel to a central axis of the inner shell.

14. The method of claim 13, wherein the instructions include:
maintaining a time, wherein the time is one or more of an actual time of day, a time of day of a most recent toggling of the at least one switch, an amount of time since the most recent toggling of the at least one switch, a time representative of a timing of a recent dosage from the pen, or a combination thereof;
recording the time; and
displaying one or more of the recorded time; a blood glucose data from a glucose sensor system, recommended doses based on therapy parameters stored in the memory, or combinations thereof.

15. A system comprising:
a pen cap for a medication delivery pen, wherein the pen cap includes:
a detector mechanism including:
an inner shell, including:
a first open end configured to receive a medication delivery pen,
a second end, and
a sidewall defined by an outer surface and an opposing inner surface, the sidewall extending between the first open end and the second end, the sidewall at least partially defining a pen-receiving cavity, and
a passageway that extends through the inner shell;
at least one switch; and
a translatable shaft at least partially disposed in the passageway and including a body that extends at least from a pen-interfacing portion in the pen-receiving cavity to a switch-interfacing portion thereof, wherein the translatable shaft is oriented to travel from a first location to at least a second location during capping of a medical delivery pen into the inner shell to toggle the at least one switch;
an analyte sensor system in communication with the pen cap, wherein the analyte sensor includes: a blood glucose meter, a flash glucose monitor, or a continuous glucose monitor,
wherein the translatable shaft is offset from and travels in a direction parallel to a central axis of the inner shell.

16. The system of claim 15, further comprising a mobile computing device, wherein the cap is in wireless communication with the mobile computing device.

17. The system of claim 16, wherein the wireless communication includes transmitting of dose timing data to a remote user interface.

18. The system of claim 16, wherein the wireless communication includes one or more of pairing the pen cap to the analyte sensor system, setting or updating therapy parameters, and sending therapy information.

19. The system of claim 18, wherein the therapy information includes one or more of capping event data, analyte data, or a combination thereof.

20. The system of claim 16, wherein the wireless communication includes sending therapy information to a cloud for one or more of analysis, updating therapy parameters, or a combination thereof.

* * * * *